(12) United States Patent
Kaula et al.

(10) Patent No.: US 9,259,577 B2
(45) Date of Patent: Feb. 16, 2016

(54) METHOD AND SYSTEM OF QUICK NEUROSTIMULATION ELECTRODE CONFIGURATION AND POSITIONING

(71) Applicant: Greatbatch Ltd., Clarence, NY (US)

(72) Inventors: Norbert Kaula, Arvada, CO (US); Scott Drees, Dallas, TX (US); Yohannes Iyassu, Denver, CO (US); Seth Kaufman, Louisville, CO (US)

(73) Assignee: Greatbatch Ltd., Clarence, NY (US)

( * ) Notice: Subject to any disclaimer, the term of this patent is extended or adjusted under 35 U.S.C. 154(b) by 64 days.

(21) Appl. No.: 13/973,316

(22) Filed: Aug. 22, 2013

(65) Prior Publication Data

US 2014/0067006 A1  Mar. 6, 2014

Related U.S. Application Data

(60) Provisional application No. 61/695,439, filed on Aug. 31, 2012, provisional application No. 61/824,296, filed on May 16, 2013.

(51) Int. Cl.
*A61N 1/36* (2006.01)
*A61N 1/372* (2006.01)
*G06F 19/00* (2011.01)

(52) U.S. Cl.
CPC ........ *A61N 1/36132* (2013.01); *A61N 1/37247* (2013.01); *G06F 19/3406* (2013.01)

(58) Field of Classification Search
CPC ................ A61N 1/37247; A61N 1/36132
USPC ..................................... 607/46, 59
See application file for complete search history.

(56) References Cited

U.S. PATENT DOCUMENTS

| | | |
|---|---|---|
| 4,432,360 A | 2/1984 | Mumford et al. |
| 5,286,202 A | 2/1994 | De Gyarfas et al. |
| 5,304,206 A | 4/1994 | Baker, Jr. et al. |

(Continued)

FOREIGN PATENT DOCUMENTS

| | | |
|---|---|---|
| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.

(Continued)

*Primary Examiner* — George Evanisko
(74) *Attorney, Agent, or Firm* — Haynes & Boone, LLP

(57) ABSTRACT

The present disclosure involves a method of determining electrode configuration and positioning for neurostimulation. A virtual representation of an implant lead is provided. The implant lead is configured to deliver electrical stimulation to a patient via one or more of a plurality of electrodes located on the implant lead. A predefined electrode activation pattern is provided. The electrode activation pattern identifies a plurality of subsets of the electrodes that can be activated one subset at a time. The electrodes in each subset are programmed with their respective electrical stimulation parameters. The subsets of the electrodes are activated one subset at a time. Each activated subset of electrodes delivers electrical stimulation to a different region of a spine of the patient.

54 Claims, 16 Drawing Sheets

(56) References Cited

U.S. PATENT DOCUMENTS

| | | | |
|---|---|---|---|
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |
| 5,628,776 A | 5/1997 | Paul et al. |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Wiedenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnett |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,826,901 B2 * | 11/2010 | Lee et al. ................ 607/59 |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Baird et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203541 A1 | 8/2007 | Goetz et al. |
| 2007/0203543 A1 | 8/2007 | Stone et al. |
| 2007/0213790 A1 | 9/2007 | Nolan et al. |

(56) References Cited

U.S. PATENT DOCUMENTS

| | | | |
|---|---|---|---|
| 2008/0004675 A1* | 1/2008 | King et al. | 607/59 |
| 2008/0033303 A1 | 2/2008 | Wariar et al. | |
| 2008/0046036 A1 | 2/2008 | King et al. | |
| 2008/0140161 A1 | 6/2008 | Goetz et al. | |
| 2008/0154340 A1 | 6/2008 | Goetz et al. | |
| 2008/0177362 A1 | 7/2008 | Phillips et al. | |
| 2008/0215119 A1 | 9/2008 | Woods et al. | |
| 2008/0218517 A1 | 9/2008 | Holmdahl | |
| 2008/0262565 A1 | 10/2008 | Bentwich | |
| 2009/0018617 A1 | 1/2009 | Skelton et al. | |
| 2009/0018619 A1 | 1/2009 | Skelton et al. | |
| 2009/0024178 A1 | 1/2009 | Hennig | |
| 2009/0048871 A1 | 2/2009 | Skomra | |
| 2009/0089034 A1 | 4/2009 | Penney et al. | |
| 2009/0099624 A1 | 4/2009 | Kokones et al. | |
| 2009/0132009 A1 | 5/2009 | Torgerson et al. | |
| 2009/0136094 A1 | 5/2009 | Driver et al. | |
| 2009/0196471 A1 | 8/2009 | Goetz et al. | |
| 2009/0196472 A1* | 8/2009 | Goetz et al. | 382/128 |
| 2009/0228070 A1* | 9/2009 | Goetz et al. | 607/59 |
| 2009/0234873 A1 | 9/2009 | Li et al. | |
| 2009/0264967 A1 | 10/2009 | Giftakis et al. | |
| 2009/0281596 A1 | 11/2009 | King et al. | |
| 2010/0004033 A1 | 1/2010 | Choe et al. | |
| 2010/0010566 A1 | 1/2010 | Thacker et al. | |
| 2010/0010574 A1 | 1/2010 | Skelton et al. | |
| 2010/0010580 A1 | 1/2010 | Skelton et al. | |
| 2010/0058462 A1 | 3/2010 | Chow | |
| 2010/0076534 A1 | 3/2010 | Mock | |
| 2010/0090004 A1 | 4/2010 | Sands et al. | |
| 2010/0106475 A1 | 4/2010 | Smith et al. | |
| 2010/0121409 A1* | 5/2010 | Kothandaraman et al. | 607/46 |
| 2010/0123547 A1 | 5/2010 | Stevenson et al. | |
| 2010/0152534 A1 | 6/2010 | Kim et al. | |
| 2010/0161345 A1 | 6/2010 | Cain et al. | |
| 2010/0198103 A1 | 8/2010 | Meadows et al. | |
| 2010/0198304 A1 | 8/2010 | Wang | |
| 2010/0222845 A1 | 9/2010 | Goetz | |
| 2010/0223020 A1 | 9/2010 | Goetz | |
| 2010/0265072 A1 | 10/2010 | Goetz et al. | |
| 2010/0268304 A1 | 10/2010 | Matos | |
| 2010/0280578 A1 | 11/2010 | Skelton et al. | |
| 2011/0004059 A1 | 1/2011 | Arneson et al. | |
| 2011/0015514 A1 | 1/2011 | Skalli et al. | |
| 2011/0015693 A1 | 1/2011 | Williamson | |
| 2011/0023343 A1 | 2/2011 | Turner et al. | |
| 2011/0038498 A1 | 2/2011 | Edgar | |
| 2011/0040546 A1 | 2/2011 | Gerber et al. | |
| 2011/0040547 A1 | 2/2011 | Gerber et al. | |
| 2011/0046697 A1 | 2/2011 | Gerber et al. | |
| 2011/0054560 A1 | 3/2011 | Rosenberg et al. | |
| 2011/0054870 A1 | 3/2011 | Dariush et al. | |
| 2011/0077459 A1 | 3/2011 | Rofougaran | |
| 2011/0077616 A1 | 3/2011 | Bennett et al. | |
| 2011/0093030 A1 | 4/2011 | Goetz et al. | |
| 2011/0093047 A1 | 4/2011 | Davis et al. | |
| 2011/0093051 A1 | 4/2011 | Davis et al. | |
| 2011/0153341 A1 | 6/2011 | Diaz-Cortes | |
| 2011/0170739 A1 | 7/2011 | Gillam et al. | |
| 2011/0172564 A1 | 7/2011 | Drew | |
| 2011/0172737 A1 | 7/2011 | Davis et al. | |
| 2011/0172744 A1 | 7/2011 | Davis et al. | |
| 2011/0185178 A1 | 7/2011 | Gotthardt | |
| 2011/0191275 A1 | 8/2011 | Lujan et al. | |
| 2011/0224523 A1 | 9/2011 | Budiman | |
| 2011/0246219 A1 | 10/2011 | Smith et al. | |
| 2011/0264165 A1 | 10/2011 | Molnar et al. | |
| 2011/0270358 A1 | 11/2011 | Davis et al. | |
| 2011/0282414 A1 | 11/2011 | Kothandaraman et al. | |
| 2011/0305376 A1 | 12/2011 | Neff | |
| 2011/0307284 A1 | 12/2011 | Thompson et al. | |
| 2011/0313268 A1 | 12/2011 | Kokones et al. | |
| 2011/0313487 A1 | 12/2011 | Kokones et al. | |
| 2012/0041518 A1 | 2/2012 | Kim et al. | |
| 2012/0046715 A1 | 2/2012 | Moffitt et al. | |
| 2012/0071947 A1 | 3/2012 | Gupta et al. | |
| 2012/0083857 A1 | 4/2012 | Bradley et al. | |
| 2012/0084689 A1 | 4/2012 | Ledet et al. | |
| 2012/0089008 A1 | 4/2012 | Strehl et al. | |
| 2012/0109230 A1 | 5/2012 | Kothandaraman et al. | |
| 2012/0192874 A1 | 8/2012 | Bolea et al. | |
| 2012/0239114 A1* | 9/2012 | Lee | 607/59 |
| 2012/0239116 A1 | 9/2012 | Lee et al. | |
| 2012/0256857 A1 | 10/2012 | Mak | |
| 2012/0265269 A1 | 10/2012 | Lui et al. | |
| 2012/0277828 A1 | 11/2012 | O'Conner et al. | |
| 2012/0290041 A1 | 11/2012 | Kim et al. | |
| 2012/0290272 A1 | 11/2012 | Bryan | |
| 2012/0290976 A1 | 11/2012 | Lahm et al. | |
| 2012/0296392 A1 | 11/2012 | Lee et al. | |
| 2012/0296396 A1 | 11/2012 | Moffitt et al. | |
| 2012/0296397 A1 | 11/2012 | Vansickle | |
| 2012/0303087 A1 | 11/2012 | Moffitt et al. | |
| 2012/0310300 A1 | 12/2012 | Kaula et al. | |
| 2013/0023950 A1 | 1/2013 | Gauthier | |
| 2013/0060299 A1 | 3/2013 | Polefko et al. | |
| 2013/0060300 A1 | 3/2013 | Polefko et al. | |
| 2013/0060301 A1 | 3/2013 | Polefko et al. | |
| 2013/0060302 A1 | 3/2013 | Polefko et al. | |
| 2013/0079848 A1 | 3/2013 | Campbell et al. | |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

Extended European Search Report issued for European Application 13182500.2 dated Nov. 7, 2013, 7 pgs.

First Examination Report issued for European Application 13182500.2 dated Aug. 24, 2015, 4 pgs.

* cited by examiner

METHOD AND SYSTEM OF QUICK NEUROSTIMULATION ELECTRODE CONFIGURATION AND POSITIONING

PRIORITY DATA

The present application is a utility application of provisional U.S. Patent Application No. 61/695,439, filed on Aug. 31, 2012, entitled "Method and System of Quick Neurostimulation Electrode Configuration and Positioning," and a utility application of provisional U.S. Patent Application No. 61/824,296, filed on May 16, 2013, entitled "Features and Functionalities of an Advanced Clinician Programmer," the disclosure of each of which is hereby incorporated by reference in its entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implanted medical devices (for example a neurostimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient.

Despite many advances made in the field of neurostimulation, one drawback is that the electronic programmers such as the clinician programmer have not been used to increase the efficiency of processes carried out during an actual implant procedure. For example, one of such processes carried out during an implant procedure involves testing pulses along the length of an implant lead, which is a device implanted next to the spinal cord containing the electrodes that deliver the electrical pulses. This process is used to determine what areas of the spinal cord need to be stimulated in order to mitigate the patient's pain, and how the lead needs to be positioned accordingly. Currently, a clinician (or another healthcare professional) would have to select one or more particular electrodes on the lead for manual programming, execute the stimulation, and wait for patient feedback. Based on the patient feedback, the clinician would have to adjust the positioning of the lead and repeat the entire process again. The process may need to be repeated several times before the clinician has found a lead position and electrode configuration that are deemed to be satisfactory. Therefore, the process discussed above is time-consuming, which is undesirable given that the process is performed in an operating room during an actual surgery. Among other things, the long process time may lead to more patient discomfort and increases the risks of the surgery. In other words, any procedure that takes place in a surgical setting is time critical. Since the lead position and electrode configuration process takes place during such surgical setting, it is imperative that it be fast, which unfortunately is not the case with existing programmers.

Therefore, although existing electronic programmers used for neurostimulation have been generally adequate for their intended purposes, they have not been entirely satisfactory in every aspect.

SUMMARY

One aspect of the present disclosure involves a system for determining electrode configuration and positioning for neurostimulation. The electronic device comprises: a memory storage component configured to store programming code; and a computer processor configured to execute the programming code to perform the following tasks: providing a virtual representation of an implant lead, the implant lead being configured to deliver electrical stimulation to a patient via one or more of a plurality of electrodes located on the implant lead; providing a predefined electrode activation pattern that identifies a plurality of subsets of the electrodes that can be activated one subset at a time, wherein the electrodes in each subset are programmed with their respective electrical stimulation parameters; and activating the subsets of the electrodes one subset at a time, wherein each activated subset of electrodes delivers electrical stimulation to a different region of a spine of the patient.

Another aspect of the present disclosure involves a medical system. The medical system includes: an implantable lead configured to deliver electrical stimulation to a patient via one or more of a plurality of electrodes located on the implantable lead; and a portable electronic programmer on which a touch-sensitive user interface is implemented, wherein the user interface is configured to: provide a virtual representation of the implantable lead; provide a predefined electrode activation pattern that identifies a plurality of subsets of the electrodes on the implantable lead that can be activated one subset at a time, wherein the electrodes in each subset are programmed with their respective electrical stimulation parameters; and activate the subsets of the electrodes one subset at a time, wherein each activated subset of electrodes delivers electrical stimulation to a different region of a spine of the patient.

Yet another aspect of the present disclosure involves a method of determining electrode configuration and positioning for neurostimulation. The method comprises: providing a virtual representation of an implant lead, the implant lead being configured to deliver electrical stimulation to a patient via one or more of a plurality of electrodes located on the implant lead; providing a predefined electrode activation pattern that identifies a plurality of subsets of the electrodes that can be activated one subset at a time, wherein the electrodes in each subset are programmed with their respective electrical stimulation parameters; and activating the subsets of the electrodes one subset at a time, wherein each activated subset of electrodes delivers electrical stimulation to a different region of a spine of the patient.

One more aspect of the present disclosure involves an electronic apparatus for determining electrode configuration and positioning for neurostimulation. The electronic apparatus comprises: input/output means for communicating with a user, the input/output means including a touch-sensitive screen configured to detect an input from the user and display an output to the user; memory storage means for storing executable instructions; and computer processor means for executing the instructions to perform the following tasks: providing a virtual representation of an implant lead, the implant lead being configured to deliver electrical stimulation to a patient via one or more of a plurality of electrodes located on the implant lead; providing a predefined electrode activation pattern that identifies a plurality of subsets of the electrodes that can be activated one subset at a time, wherein the electrodes in each subset are programmed with their respective electrical stimulation parameters; and activating the subsets of the electrodes one subset at a time, wherein each activated subset of electrodes delivers electrical stimulation to a different region of a spine of the patient.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

Figure 1:
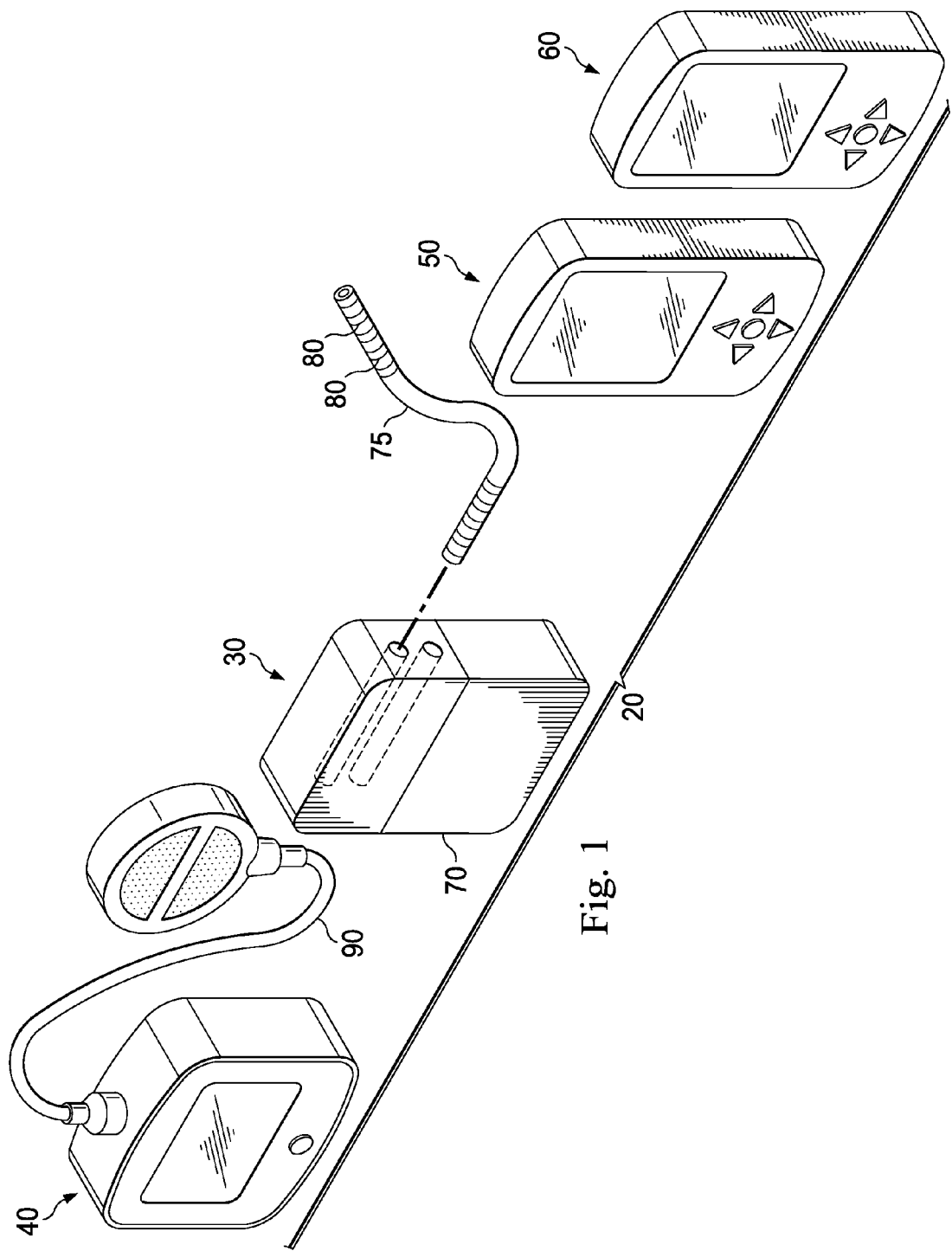
FIG. 1 is a simplified block diagram of an example medical environment in which evaluations of a patient may be conducted according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

The use of active implanted medical devices has become increasingly prevalent over time. Some of these implanted medical devices include neurostimulator devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

In recent years, these electronic programmers have achieved significant improvements, for example, improvements in size, power consumption, lifetime, and ease of use. Despite these advances, electronic programmers have not been used to increase the efficiency of performing certain procedures in the field of neurostimulation. For instance, healthcare professionals may need to perform a process of testing electrode patterns for implant lead positioning to determine the exact placement of an implant lead. In more detail, during/after the lead implantation, the healthcare professional programs pulses on the clinician programmer. This programming includes a set of the electrodes picked by the healthcare professional from experience or by guessing (which electrodes are to be anodes and cathodes and in what time sequence). After the pulses have been programmed, the healthcare professional activates stimulation using the clinician programmer. The patient gives feedback regarding the effect of the stimulation verbally, and the healthcare professional adjusts the position of the lead or the electrode set accordingly. The patient continues giving feedback, and the healthcare professional continues adjusting the pattern and positioning until the results are satisfactory (e.g., pain is minimized). However, this is a time-consuming process that takes place during actual surgery, which is undesirable. In general, any procedure that takes place in a surgical setting is time critical (i.e., needs to be performed fast). A long time delay during surgery may increase surgery risks and/or patient discomfort. Since the lead position and electrode configuration process discussed above takes place during such surgical setting, a versatile electronic programmer should be able to perform this process very quickly. Unfortunately, existing programmers have not been able to offer a satisfactory solution to perform such process quickly.

To address the issues discussed above, the present disclosure offers a method and system of quick neurostimulation electrode configuration and positioning via an electronic programmer such as the clinician programmer, as discussed below in more detail.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2-3 and 5-7 illustrate an example user interface 100 of an embodiment of the clinician programmer 60. The user interface 100 is intended for a target user, which may be a healthcare professional, for example a surgeon. The user and the healthcare professional are interchangeably referred to in the following paragraphs, but it is understood that they need not necessarily be the same entity.

Figure 2:
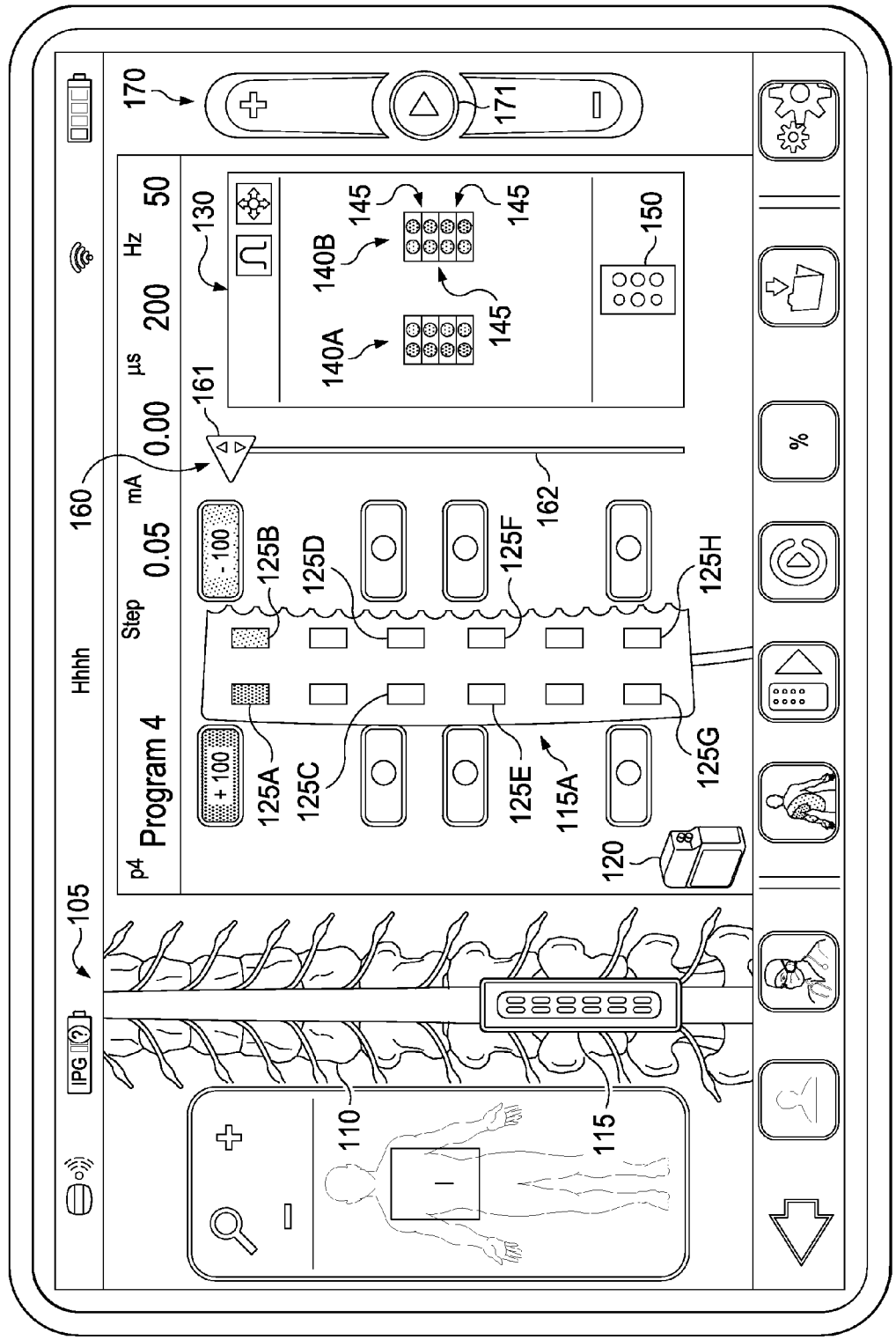
FIGS. 2, 3A-3D, and 5-7 are embodiments of a user interface for determining electrode configuration and positioning for neurostimulation according to various aspects of the present disclosure.

Referring to FIG. 2, the user interface 100 displays a virtual representation of an anatomical environment 105 in which a lead is implanted. In the illustrated embodiment, the anatomical environment 105 includes a virtual representation of a portion of a spine 110 (representing the spine of the patient undergoing the surgery), as well as a virtual representation of a lead 115 shown with respect to the spine 110. The lead 115 may be an embodiment of the lead 75 shown in FIG. 1, or any other suitable implantable lead. The anatomical environment 105 also includes a virtual representation of an implantable pulse generator 120 as an embodiment of the implantable medical device 30 shown in FIG. 1.

The user interface 100 also illustrates another virtual representation of the lead 115A in greater detail. For example, the lead 115A is a 2×6 lead and contains two columns and six rows of electrodes 125. Each of the electrodes 125 can be individually programmed with its own set of stimulation parameters in order to deliver electrical stimulation to a nearby nerve tissue. These stimulation parameters include, but are not limited to, electrical current amplitude, pulse width, frequency, and electrode polarity (anode/cathode).

The user interface 100 further illustrates an electrode pattern menu 130 (also referred to an electrode pattern library). The menu 130 contains a plurality of preset or predefined electrode activation patterns 140, such as patterns 140A and 140B shown herein. The electrode activation patterns 140 each identify a plurality of subsets of the electrodes 125 that are to be activated one subset at a time (discussed in more detail below). In the illustrated embodiment, the electrode activation pattern 140A is selected, which corresponds to four subsets of electrodes 125 on the lead 115 to be activated: electrodes 125A and 125B as a first subset, electrodes 125C and 125D as a second subset, electrodes 125E and 125F as a third subset, and electrodes 125G and 125H as a fourth subset. To clearly illustrate which electrodes 125 belong to which subset, the subsets of electrodes 125 are segregated from one another with virtual dividers (illustrated herein as lines) 145 in the user interface 100.

As discussed above, the electrodes 125 in each subset may be programmed with their own stimulation parameters. The stimulation parameter programming may be set as default values by the user interface 100 in some embodiments. In other embodiments, a user may enter in the stimulation parameters through a different part of the user interface, for example in accordance with U.S. patent application Ser. No. 13/601,631, filed on Aug. 31, 2012, and entitled "Programming and Virtual Reality Representation of Stimulation Parameter Groups" to Norbert Kaula, et al., the contents of which are hereby incorporated by reference in its entirety. It is understood that the stimulation parameters may be set before surgery (to implant the lead) takes place, or they may be set or adjusted during surgery. In certain embodiments, the stimulation parameters may also be set or adjusted post-surgery, for example in a follow-up visit. Some of these stimulation parameters may also be displayed in the user interface 100 as text. The electrode polarity of each electrode may be indicated by a particular color, for example blue for a cathode and green for an anode, or vice versa.

It is understood that the electrodes 125 included in the electrode activation patterns 140 may not necessarily include all the available electrodes 125 on the lead 115A. For example, in the illustrated embodiment, though the lead 115A includes a total of twelve electrodes, only eight of such electrodes 125A-125H are identified in the electrode activation patterns 140A and 140B. This is done to save precious testing time in an electrode configuration and positioning process discussed below. In some embodiments, the subsets of electrodes identified by the electrode activation patterns 140 are spaced apart from adjacent subsets as much as feasible. In this manner, the subsets of electrodes 125 may still "cover" the length of the lead 115 with a minimum number of electrodes.

In certain embodiments, some of the electrode activation patterns may be set up so that only electrodes from a limited portion (e.g., the top half) of the lead 115A are included. These patterns may be referred to as "partial" patterns and may be useful in carrying out a "refined" or "detailed" testing of the electrodes 125. For example, a "coarse" pattern such as the electrode activation pattern 140A may be used to carry out a "coarse" testing, which may reveal that the target nerve tissue is covered by the top half of the lead 115A, but it is not known exactly which electrodes 125 best cover the target nerve tissue. Thereafter, a "refined" testing is performed using the "partial" pattern that includes all the electrodes located in the top half of the lead 115A. The "partial" pattern may still divide the electrodes into multiple subsets, for example three subsets. The "refined" testing steps through each subset of electrodes and consequently will identify which subset of electrodes offer the best coverage of the target nerve tissue.

It is understood that the selection of each electrode activation pattern 140 may be done by a touch-sensitive user input, for example by a user (e.g., healthcare professional) touching an area of the display on the clinician programmer illustrating the pattern 140. Alternatively, the electrode pattern menu 130 may further include a virtual toggle mechanism 150 that allows the selection of a desired pattern 140 by toggling among a plurality of available patterns 140. For example, if two patterns 140A and 140B exist, and the pattern 140A is currently selected, then a "click" of the virtual toggle mechanism 150 changes the current selection of the pattern to 140B, and vice versa. It is understood, however, that the virtual toggle mechanism 150 allows the more than just two patterns to be iterated. For example, in some embodiments, the virtual toggle mechanism 150 may be used to toggle through four or five (or more) patterns iteratively.

The user interface 100 illustrates a virtual control mechanism 160 for controlling the activation of the subsets of electrodes 125. In the illustrated embodiment, the virtual control mechanism 160 includes a slider 161 that can be dragged up and down a bar 162. The user (e.g., healthcare professional) may use his/her finger to engage the virtual control mechanism 160, for example to move the slider 161 to different positions on the bar 162. Different positions of the slider 161 on the bar 162 correspond to different subsets of electrodes 125 being selected on the lead 115A. Therefore, as the user moves the slider 161 along the bar 162, different subsets of electrodes 125 are selected, meaning that they are now ready to be activated to begin delivering electrical stimulation to the patient's body.

To initiate the activation of electrodes, the user interface 100 employs a virtual activation mechanism 170. The virtual activation mechanism 170 includes a "run" button 171, which if pressed by the user will activate the selected subset of electrodes 125 (also referred to as electrode subsets). In other words, the engagement of the "run" button 171 causes the selected subset of electrodes 125 to begin delivering electrical stimulation to nearby nerve tissue. In the illustrated embodiment, the virtual activation mechanism 170 further includes a "+" toggle and a "−" toggle, which may be used to adjust the programming value of stimulation parameters such as electrical current, etc.

Figure 3A:
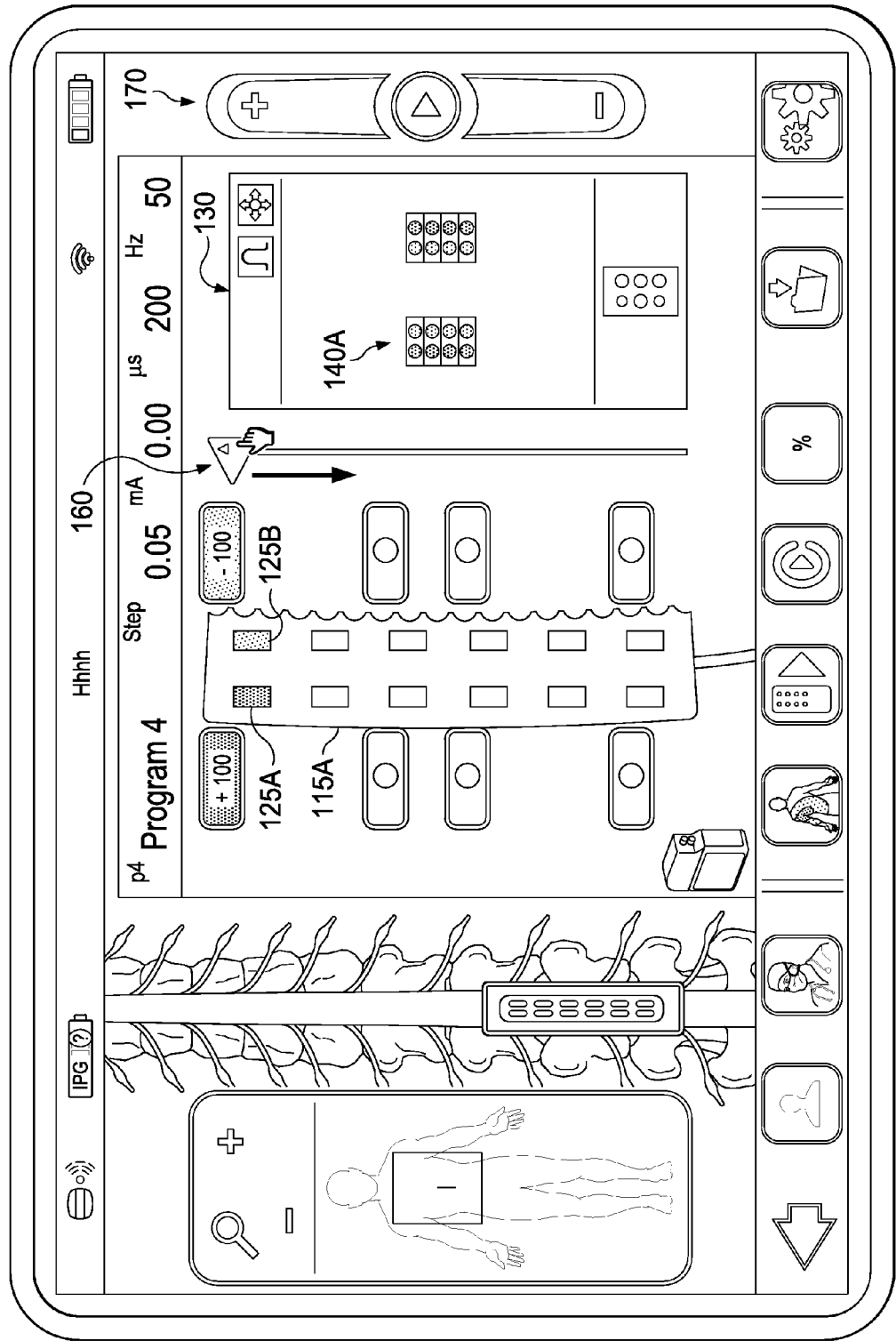

FIGS. 3A-3D illustrate an example of activating the subsets of electrodes using the virtual control mechanism 160. Referring to FIG. 3A, the electrode activation pattern 140A is selected from the electrode pattern menu 130 by a user, for example through a touch-sensitive input. The initial position of the virtual control mechanism 160 (i.e., the slider tool) is at the top, which corresponds to the selection of the electrodes 125A and 125B that are located at the top of the lead 115A. In the illustrated embodiment, the electrodes 125A and 125B are programmed with their own stimulation parameters (e.g., current, pulse width, frequency, etc.), and one of the electrodes 125A is programmed to be an anode, and the other one is programmed to be a cathode. The user may then activate the electrodes 125A and 125B by pressing the "run" button on the virtual activation mechanism 170. The activated electrodes 125A and 125B will deliver electrical stimulation to nearby nerve tissue.

Figure 3B:
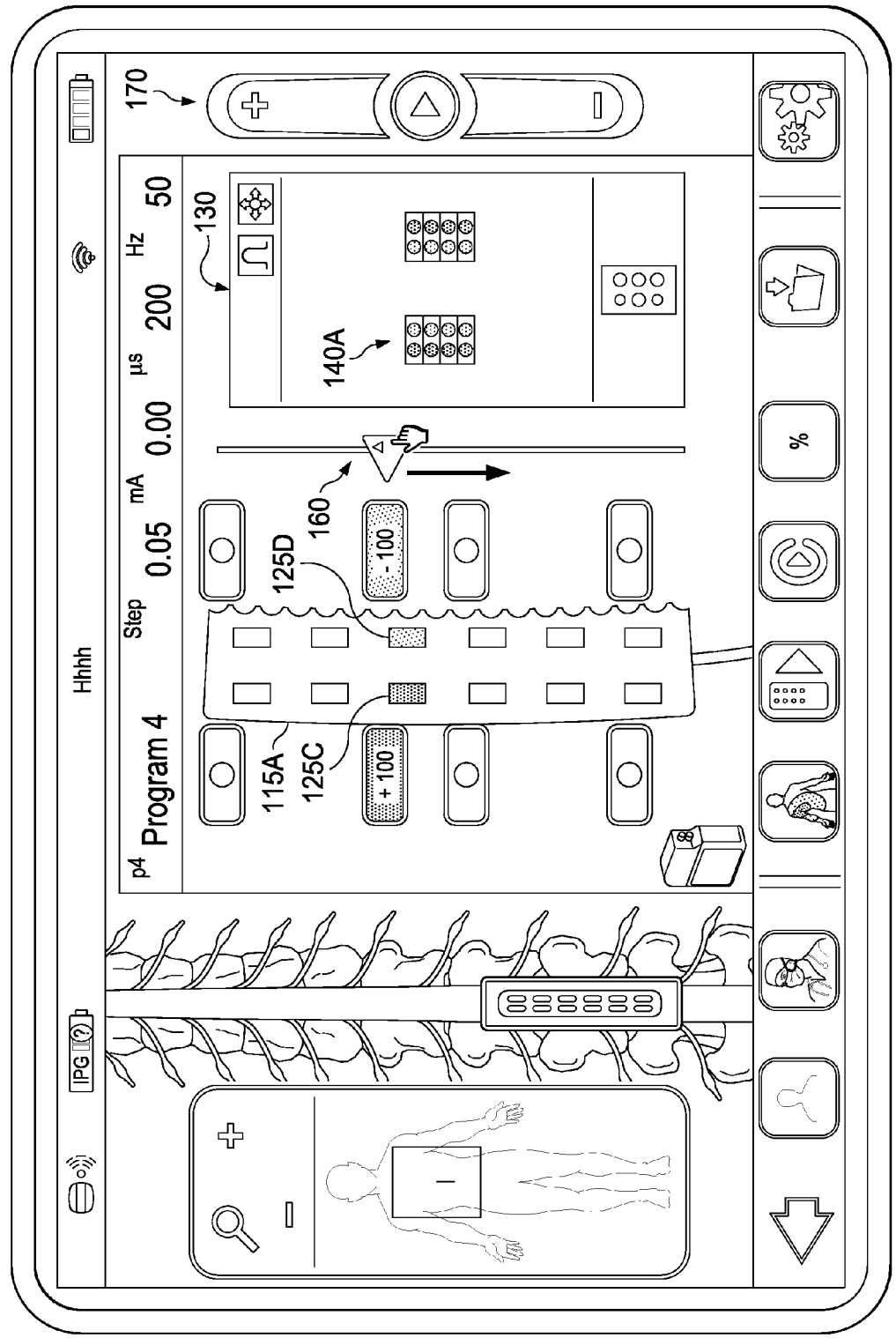

Referring now to FIG. 3B, the user slides the slider of the virtual control mechanism 160 downward, and consequently the electrodes 125C and 125D on the lead 115A become selected. The electrodes 125C and 125D are programmed with their own stimulation parameters, which may or may not be the same as the electrodes 125A and 125B, respectively. Again, the user may then activate the electrodes 125C and 125D by pressing the "run" button on the virtual activation mechanism 170. The activated electrodes 125C and 125D will deliver electrical stimulation to nearby nerve tissue.

Figure 3C:
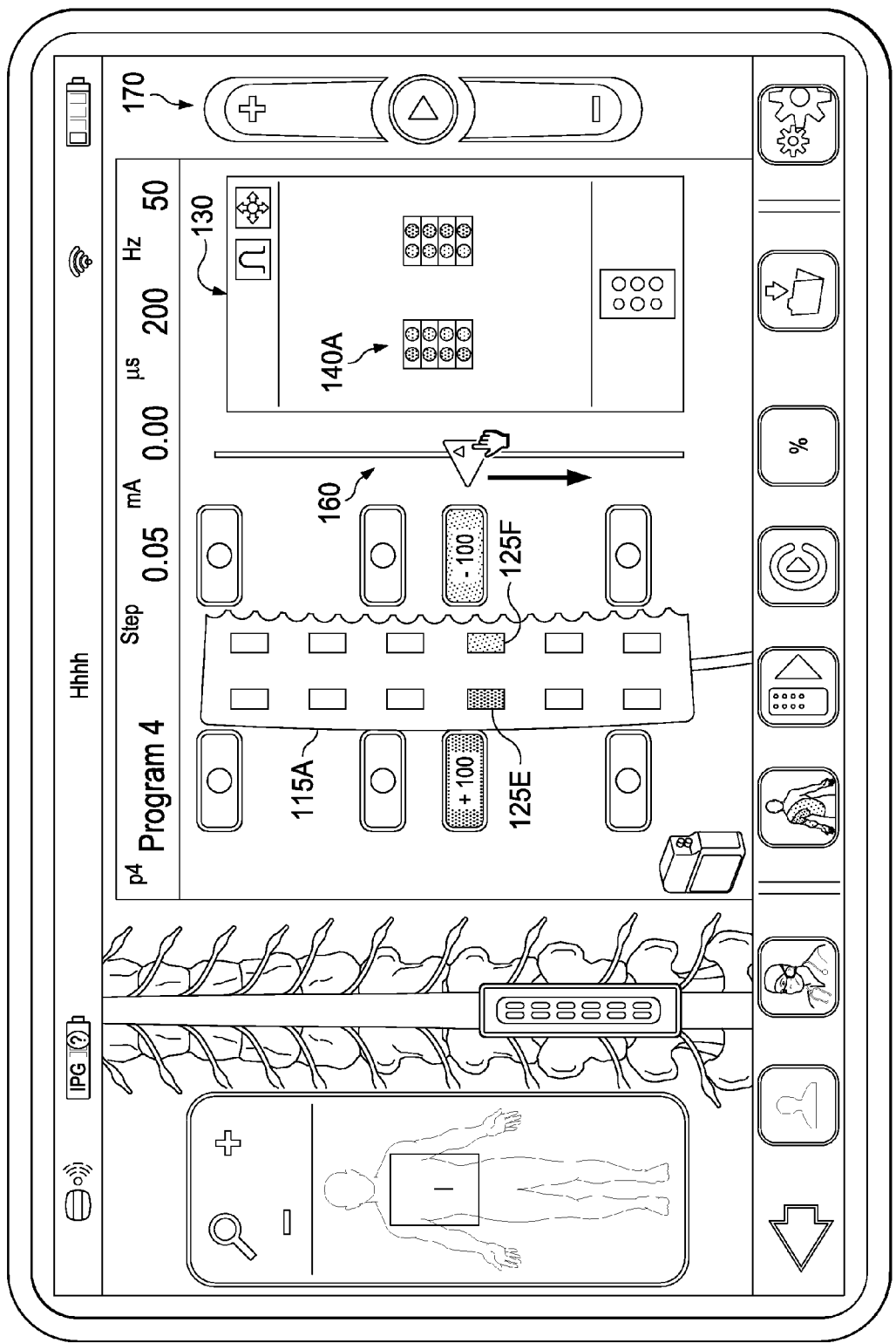

Referring now to FIG. 3C, the user slides the slider of the virtual control mechanism 160 further downward, and consequently the electrodes 125E and 125F on the lead 115A become selected. The electrodes 125E and 125F are programmed with their own stimulation parameters, which may or may not be the same as the electrodes 125A and 125B or 125C and 125D, respectively. Again, the user may then activate the electrodes 125E and 125F by pressing the "run" button on the virtual activation mechanism 170. The activated electrodes 125E and 125F will deliver electrical stimulation to nearby nerve tissue.

Figure 3D:
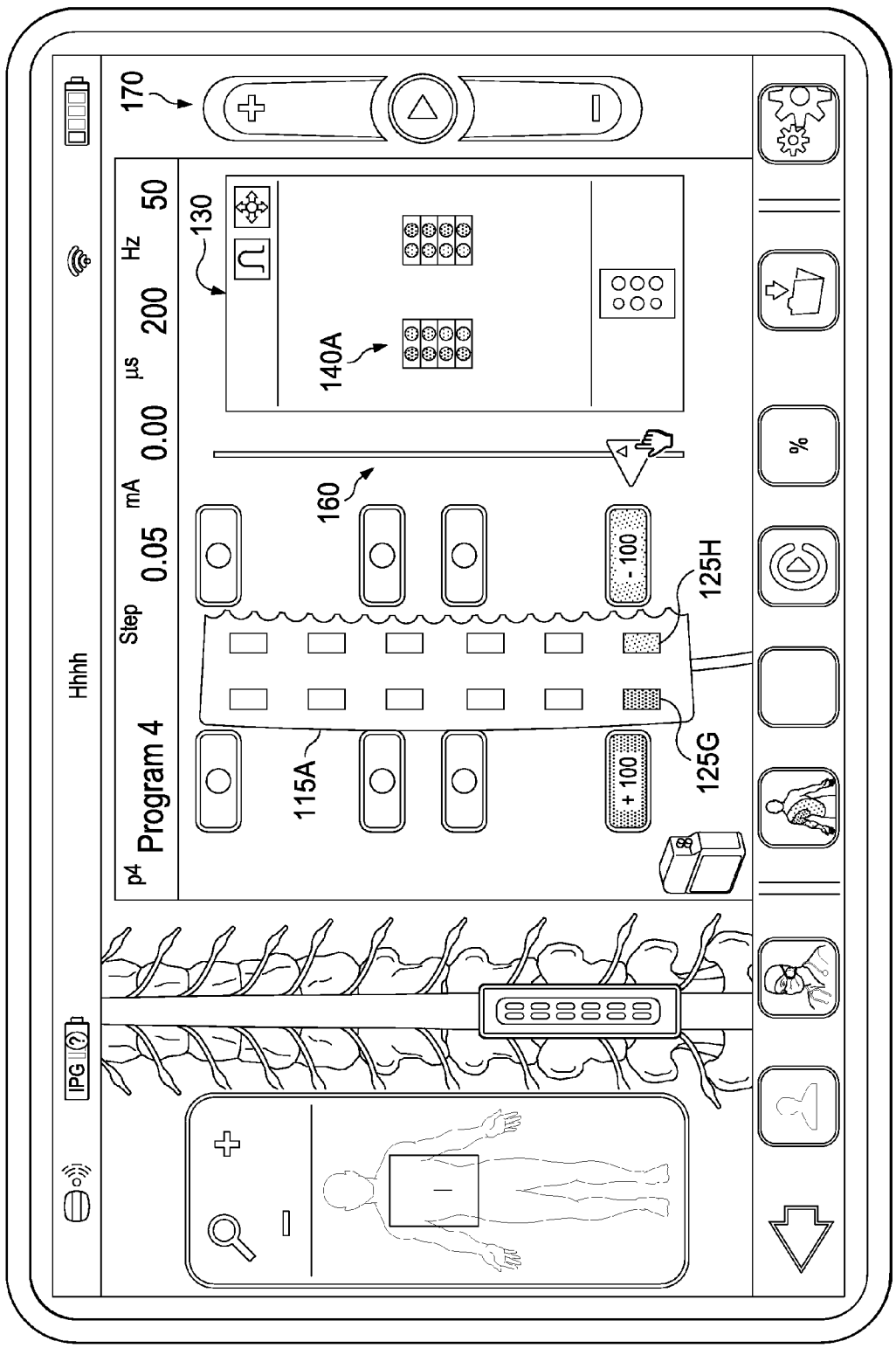

Referring now to FIG. 3D, the user slides the slider in the virtual control mechanism 160 downward again, and consequently the electrodes 125G and 125H on the lead 115A become selected. The electrodes 125G and 125H are programmed with their own stimulation parameters, which may or may not be the same as the electrodes 125A and 125B, 125C and 125D, or 125E and 125F, respectively. Again, the user may then activate the electrodes 125G and 125H by pressing the "run" button on the virtual activation mechanism 170. The activated electrodes 125G and 125H will deliver electrical stimulation to nearby nerve tissue.

Figure 4:
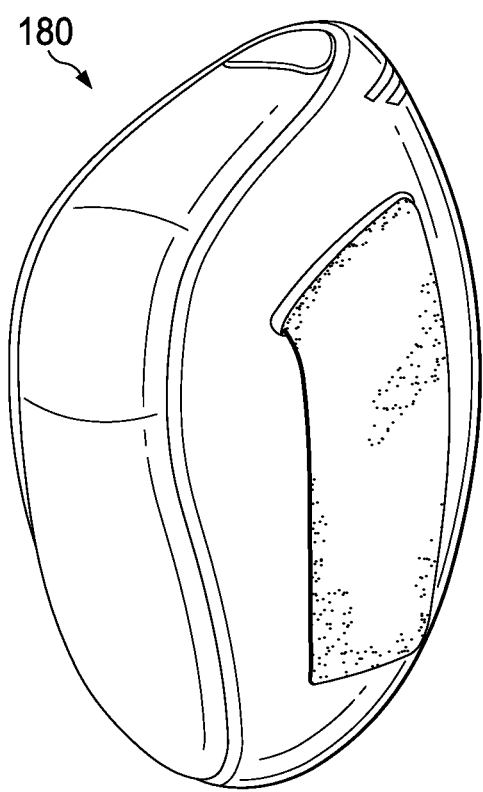
FIG. 4 is a simplified illustration of an electronic patient feedback device.

During the electrode configuration and positioning process described above with reference to FIGS. 3A-3D, the patient may provide feedback verbally or with a patient feedback tool 180, an embodiment of which is illustrated in FIG. 4. The patient feedback tool 180 (also referred to as a patient feedback device) is a portable hand held device and is sensitive to pressure. The patient may squeeze the patient feedback tool 180 more or less to convey the level of pain reduction they experience in response to the delivered electrical stimulation. In some embodiments, the patient feedback tool 180 may also be calibrated for each patient before surgery to take into account of that particular patient's strength and grip. Additional aspects and other embodiments of the patient feedback tool 180 are described in more detail in U.S. Patent Application No. 2012/0310305, filed on May 31, 2011, and entitled "Patient handheld device for use with a spinal cord stimulation system" to Kaula, et al., the disclosure of which is hereby incorporated by reference in its entirety. It is understood, however, that the patient feedback tool 180 is used herein merely as an example mechanism for providing and obtaining patient feedback. In other embodiments, other suitable tools and devices may be used to obtain a pressure-based feedback, or different forms of feedback, such as verbal feedback. After the activation of the subsets of electrodes 125 according to the pattern 140A, the healthcare professional considers the patient feedback and may adjust the physical location of the actual implanted lead (represented by the virtual lead 115A). This adjustment is done during the implant surgery. In addition, the healthcare professional may also tweak the stimulation parameters of one or more of the electrodes 125.

Figure 5:
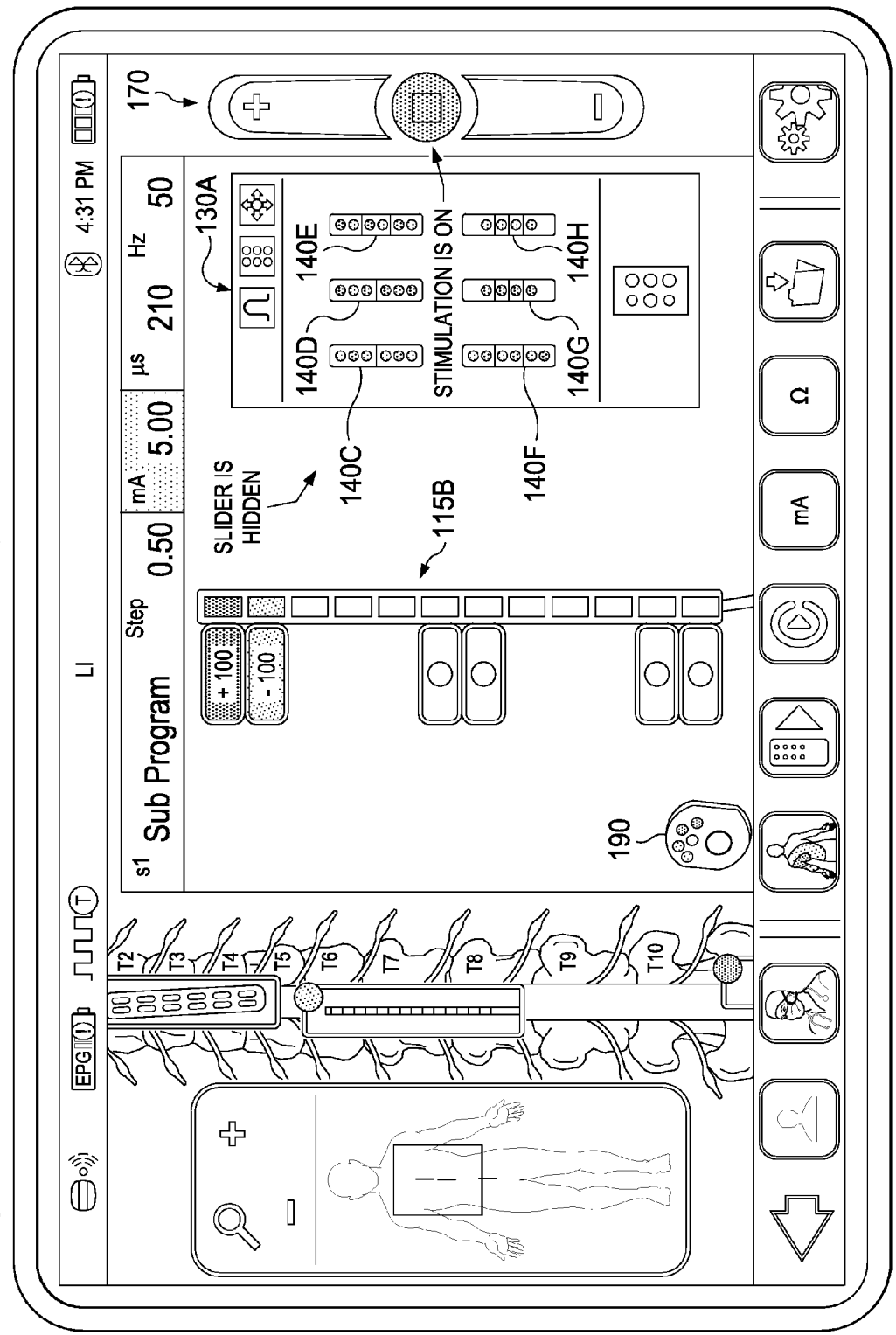

It is understood that, if electrical stimulation is still turned on while the virtual control mechanism 160 is being used to change electrode positions (i.e., selecting different subsets of electrodes for activation), the patient may feel discomfort or pain, particularly if the different subsets of electrodes are located relatively far away from one another, and thus moving down the "slider" (i.e., the virtual control mechanism 160) will trigger electrodes to deliver pulses in regions of the body where no pain is felt and no stimulation is needed. Hence, as a safety control feature, the user interface 100 hides the virtual control mechanism 160 while electrical stimulation is on, as shown in FIG. 5. It is only when electrical stimulation is turned off (such as shown in FIGS. 3A-3D) that the virtual control mechanism 160 will become visible again.

FIG. 5 also illustrates another electrode pattern menu (or library) 130A that includes a plurality of other example electrode activation patterns 140C-140H. These electrode activation patterns 140C-140H are defined with respect to a single column 1×12 implant lead 115B, which contains twelve electrodes. Again, each of the electrode activation patterns 140C-140H correspond to different subsets of the electrodes on the lead 115B being selectable and activatable, and the electrodes may each have their own stimulation parameters. In situations where all of the electrodes are configured to be anodes (or cathodes), such as in the electrode activation patterns 140G and 140H, an enclosure 190 (also referred to as a "can") or grounding wire (not illustrated) may be used to balance the stimulation current.

It is understood that the part of the user interface 100 used to accomplish the electrode configuration and positioning process discussed above is not limited to what is shown in FIGS. 2, 3 and 5. Rather, the user interface 100 may contain additional features and/or may implement the features described above differently. For example, though the virtual control mechanism 160 manifests itself as a "slider tool" in the illustrated embodiments, a virtual joystick, a virtual toggle, or a virtual switch may also be used to implement the virtual control mechanism. As another example, in some embodiments, a virtual button or toggle can be implemented in the user interface 100 to reverse the polarity of all the electrodes, so that all cathodes will become anodes, and all anodes will become cathodes. As a further example, the user interface 100 may be configured to let the user simply click on the electrode subsets of interest directly on the lead 115 to select these electrode subsets, thereby bypassing the use of the virtual control mechanism 160. As yet another example, the electrode pattern menu 130 may be obviated in some embodiments. Instead, a plurality of leads similar to the lead 115A/115B may be displayed side by side (space permitting). Each of the displayed lead may have a clear indication of what the activatable subsets of electrodes are. Thus, to select a desired electrode configuration pattern, the healthcare professional (or any other user) simply needs to click on a particular lead among the several displayed leads.

Figure 6:
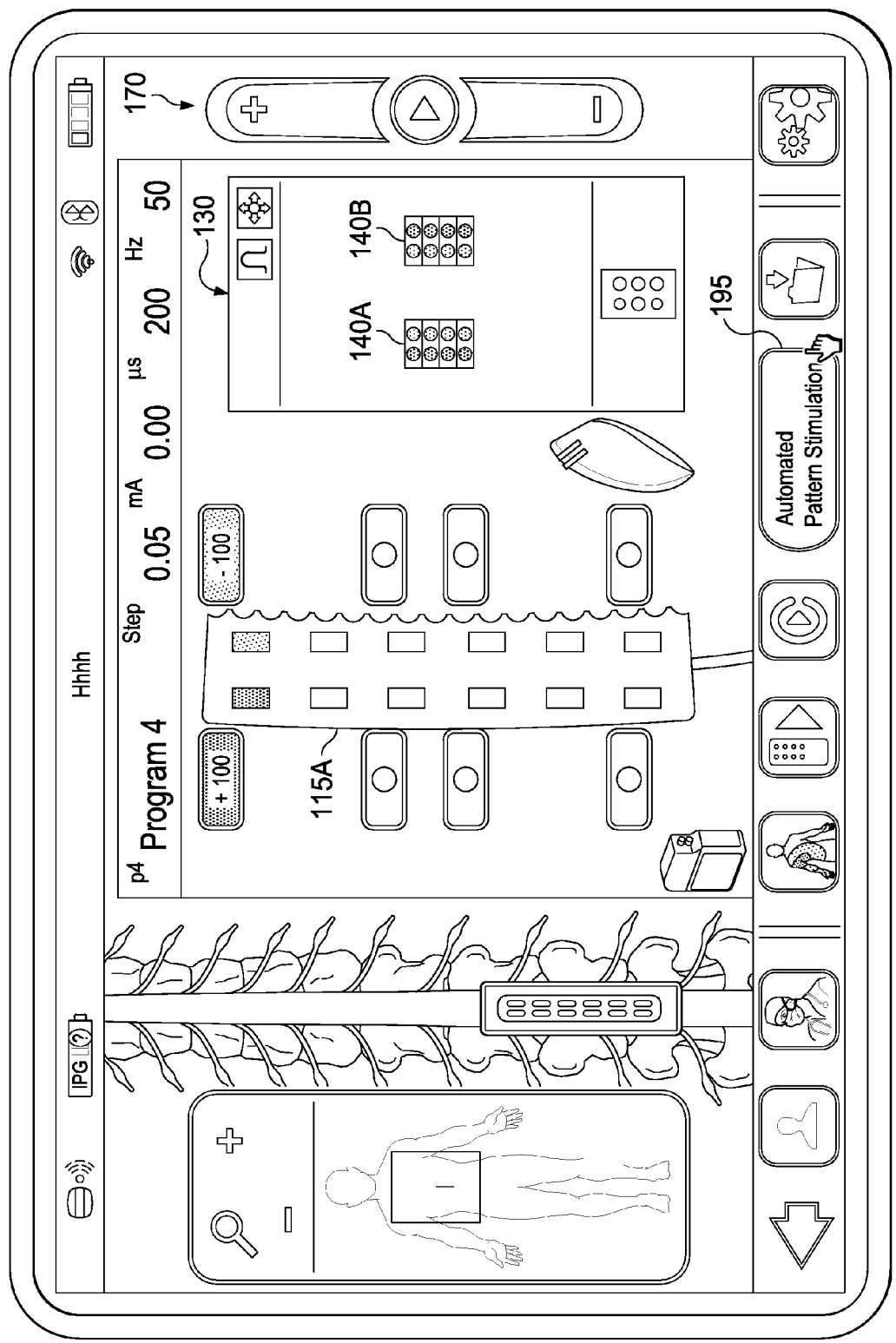
Figure 7:
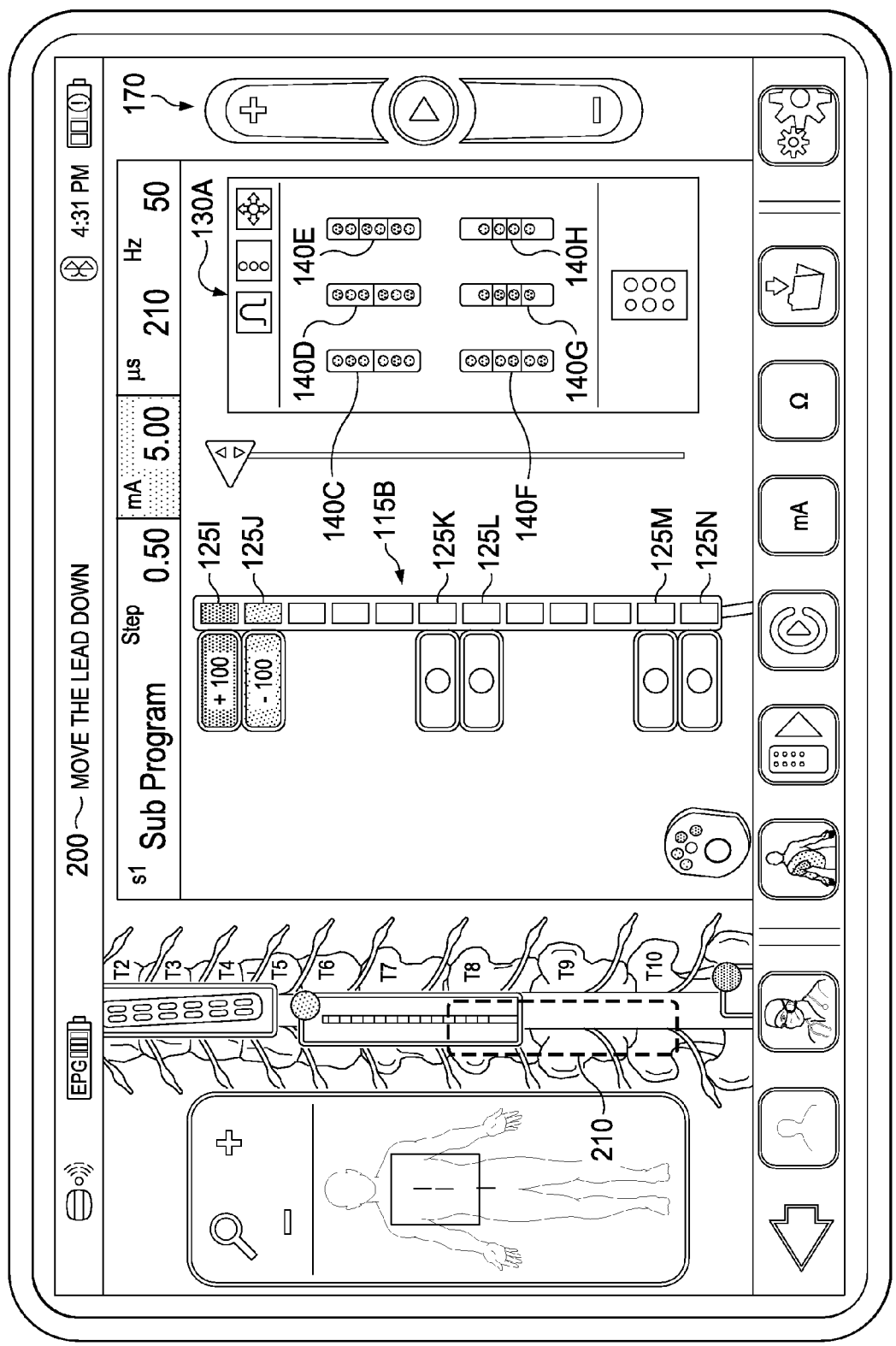

The electrode configuration and positioning process discussed above may also be performed automatically without using the virtual control mechanism 160. For example, referring now to FIG. 6, the subsets of electrodes 125 in an electrode activation pattern 140 may be selected and activated automatically with pauses between the activation of each electrode subset for patient feedback, which may be provided using the patient feedback tool 180 or other types of feedback. The user selects a lead 115A and an electrode activation pattern 140 to apply to the lead 115A, and then an automated pattern stimulation option 195 is selected, as shown in FIG. 6. In this example, the subset of electrodes located in the top of the lead 115A is activated until the patient squeezes the patient feedback tool 180 or a timeout has occurred. Thereafter, the pattern is shifted to the next position (i.e., the subset of electrodes below the top electrodes are selected and activated). This process repeats until all the electrode subsets identified by the pattern 140 have been covered. The patient may signal depth or lack of stimulation (or different degrees of pain reduction) by applying different amounts of force to the patient feedback tool 180. For example, stimulation not being felt can be signaled by no squeeze, any stimulation felt can be signaled by a medium squeeze, and painful stimulation can be signaled by a hard squeeze.

In some embodiments, the user interface 100 may also be able to provide a recommendation as to repositioning of the lead 115. For example, referring to FIG. 7, an electrode configuration and positioning process as discussed above has been performed using the electrode activation pattern 140E. Suppose that, of all the electrode subsets tested, the subset consisting of electrodes 125M and 125N offered the patient the greatest pain reduction. In terms of providing neurostimulation, one or two electrodes may be sufficient to provide the necessary electrical stimulation to the target nerve tissue. Thus, if the lead 115B is implanted as is in the patient, the electrodes 125M and 125N will be able to offer the patient the desired neurostimulation to reduce the pain.

However, as a practical matter, the position of the lead 115B may shift after implantation, which may occur over time as the patient moves his/her body. Even a small positional shift of the lead may cause the target nerve tissue to fall outside the coverage area of the electrodes 125M and 125N. Therefore, to ensure effective coverage and to create redundancy, the lead 115B (as well as nearly all other types of leads) includes a plurality of electrodes that span a greater distance, so as to account for the future potential positional shift of the lead 115B. It may be desirable to implant the lead 115B in a manner such that its center electrodes (e.g., 125K and 125L) are positionally-aligned with the target nerve tissue, once the target nerve tissue is identified through the electrode configuration and positioning process discussed above.

In the example discussed herein, the target nerve tissue is located proximate to the current implant position of the electrodes 125M and 125N. Therefore, in order to ensure redundancy, the center electrodes 125K and 125L should be repositioned proximate to (or until they are aligned with) such target nerve tissue. In some embodiments, the user interface 100 may display a text-based recommendation 200 to the user, which may state "MOVE THE LEAD DOWN" to let the user know that the lead 115B needs to be repositioned downward along the spine to achieve the desired redundancy. The recommendation 200 may be even more specific and may state "MOVE THE LEAD DOWN 3 CENTIMETERS" as an example. The repositioning distance may be calculated as a function of the length of the lead 115B. In embodiments where more than one column of electrodes is used in a lead, the recommendation may also include a recommended shift to the left or to the right. In some other embodiments, the recommendation may be verbally announced to the user rather than being displayed as text.

In addition to, or instead of displaying the text-based recommendation 200 (or verbally announcing the recommendation), the user interface 100 may also graphically display a recommended location for the lead. In the embodiment shown in FIG. 7, the recommended location for the lead is illustrated as an outline contour 210 of the lead. The recommended location for the outline contour 210 is calculated in response to patient feedback and the geometries (e.g., length and/or width) of the lead. Since the outline contour 210 is graphically overlaid on top of particular segments of the spinal cord (e.g., C1-C7 for the top 7 vertebrae of the cervical region, T1-C12 for the next 12 vertebrae of the thoracic region, L1-L5 for the final 5 vertebrae of the lumbar region, and S1-S5 for the 9 fused vertebrae of the sacrococcygeal region), the healthcare profession will know exactly where to reposition the lead so that the center of the lead is aligned with the target nerve tissue.

Figure 8:
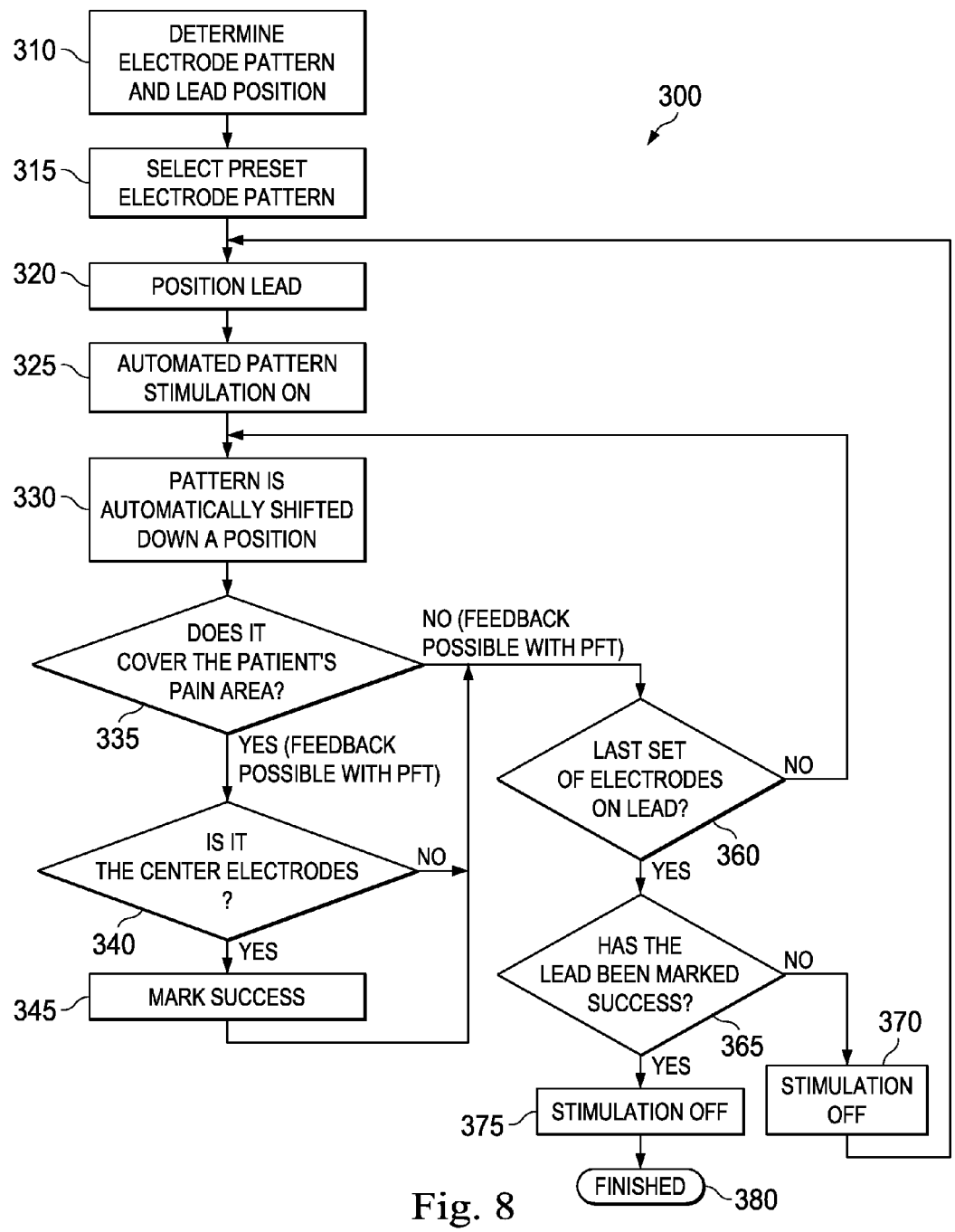
FIGS. 8-9 are simplified flowcharts illustrating a method of determining electrode configuration and positioning for neurostimulation according to various aspects of the present disclosure.

FIG. 8 is a simplified flowchart of a method 300 of determining electrode configuration and positioning for neurostimulation according to various aspects of the present disclosure. The method 300 includes a step 310 to initiate the determination of electrode pattern and lead position. The method 300 continues to a step 315, in which a preset electrode pattern is selected. The method 300 continues to a step 320, in which a lead is positioned. The method 300 continues to a step 325, in which the automated pattern stimulation is turned on. The method 300 continues to a step 330, in which the pattern is automatically shifted down a position. The method 300 continues to a decision step 335 to determine whether the patient's pain area is covered. If the answer to the decision step 335 is yes, the method 300 proceeds to another decision step 340 to determine whether it is the center electrodes on the lead. If the answer is yes, then the method 300 continues to a step 345 where the lead is marked a success. If the answer from the decision step 340 is no, then the method 300 proceeds to another decision step 360 (discussed below).

If the answer from the decision step 335 is no (or if the answer from the decision step 340 is no), then the method 300 continues to a decision step 360 to determine whether the last set of electrodes on the lead has been reached. If the answer from the decision step 360 is no, the method 300 proceeds to step 330. If the answer from the decision step 360 is yes, then the method 300 proceeds to another decision step 365 to determine whether the lead has been marked a success. If the answer from the decision step 365 is no, then the method 300 proceeds to a step 370 to turn stimulation off and thereafter proceeds to the step 320. If the answer from the decision step 365 is yes, then the method 300 continues to a step 375 to turn stimulation off. The method 300 concludes at step 380.

Figure 9:
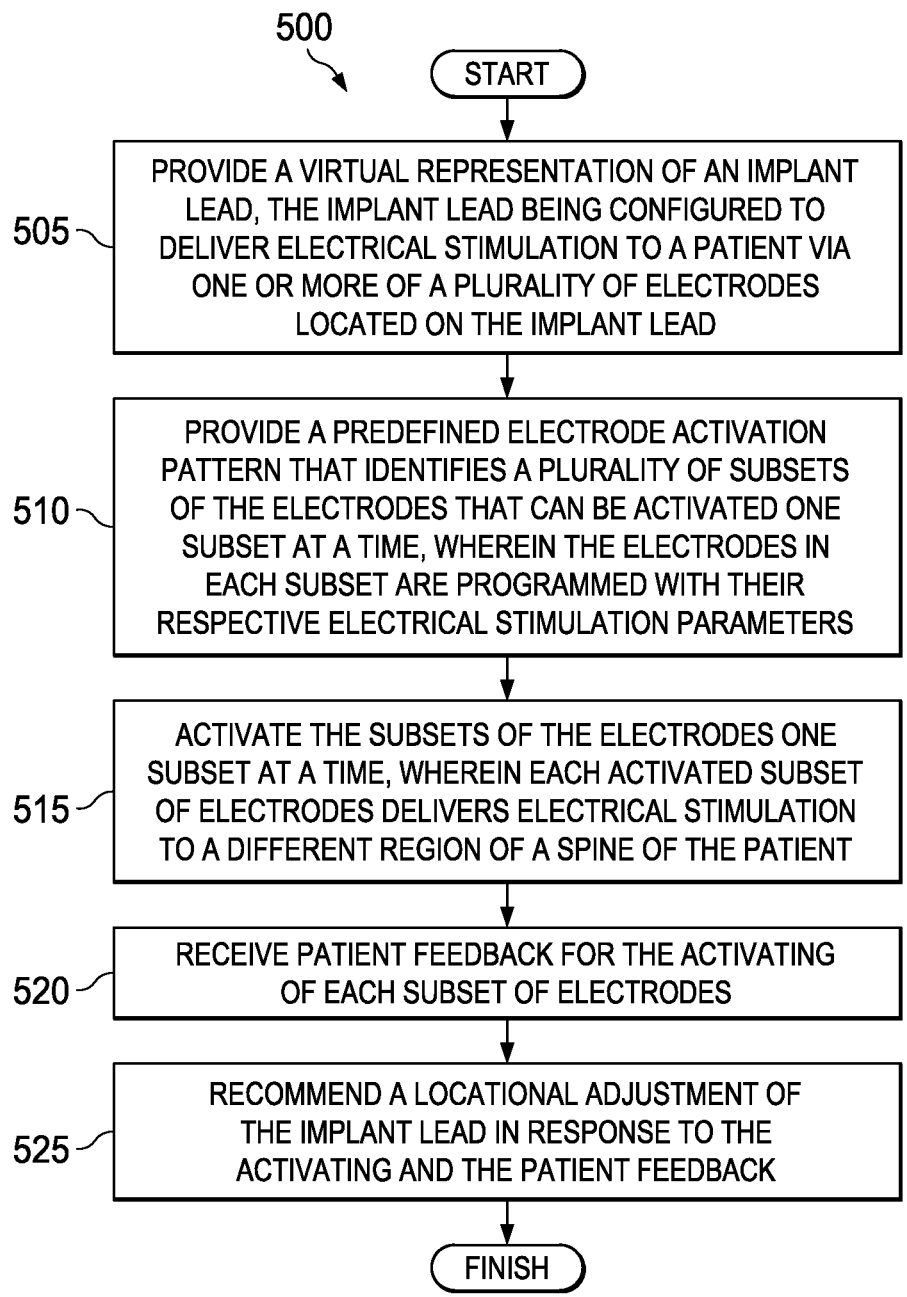

FIG. 9 is a simplified flowchart of a method 500 of determining electrode configuration and positioning for neurostimulation according to various aspects of the present disclosure. The method 500 includes a step 505, in which a virtual representation of an implant lead is provided. The implant lead is configured to deliver electrical stimulation to a patient via one or more of a plurality of electrodes located on the implant lead.

The method 500 includes a step 510, in which a predefined electrode activation pattern is provided. The electrode activation pattern identifies a plurality of subsets of the electrodes that can be activated one subset at a time. The electrodes in each subset are programmed with their respective electrical stimulation parameters. In some embodiments, the electrical stimulation parameters include at least one of: current amplitude, pulse width, frequency, or electrode polarity. In some embodiments, the step 510 is performed such that the different subsets of electrodes are segregated by virtual dividers on the virtual representation of the implant lead. In some embodiments, the electrode activation pattern is provided as a part of a pattern library containing a plurality of different predefined electrode activation patterns.

In some embodiments, the steps 505 and 510 include simultaneously displaying the virtual representation of the implant lead and the predefined electrode activation pattern on a screen of a clinician programmer. The method 500 may also include a step of displaying, on the screen of the clinician programmer, a virtual representation of an anatomical environment containing a portion of the spine of the patient and a disposition of the implant lead with respect to the portion of the spine.

The method 500 includes a step 515, in which the subsets of the electrodes are activated one subset at a time. Each activated subset of electrodes delivers electrical stimulation to a different region of a spine of the patient. In some embodiments, the step 515 is performed during a surgery that implants the implant lead into the patient. In some embodiments, the step 515 includes automatically activating the subsets of the electrodes according to a plurality of predefined sequence steps. A different subset of electrodes is activated at each sequence step. In some embodiments, the subsets of electrodes are activated consecutively along a direction.

The method 500 includes a step 520, in which patient feedback is received for the activating of each subset of electrodes. The patient feedback may be received via an electronic patient feedback tool or by verbal communication.

The method 500 includes a step 525, in which a locational adjustment of the implant lead is recommended in response to steps 515 and 520. In some embodiments, the step 525 includes: identifying, based on the patient feedback, a region of the spine that offers the most pain reduction for the patient; and recommending the locational adjustment of the implant lead in a manner such that one or more electrodes located near a center of the implant lead are aligned with the region of the spine that offers the most pain reduction for the patient.

It is understood that additional process steps may be performed before, during, or after the steps 505-525. For example, the method 500 may further include a step of displaying a virtual control mechanism and a step of detecting, from a user, an engagement of the virtual control mechanism. The activating the subsets of electrodes may be performed in response to the detected engagement of the virtual control mechanism. In some embodiments, the virtual control mechanism includes one of: a virtual slider, a virtual toggle, or a virtual joystick.

Figure 10:
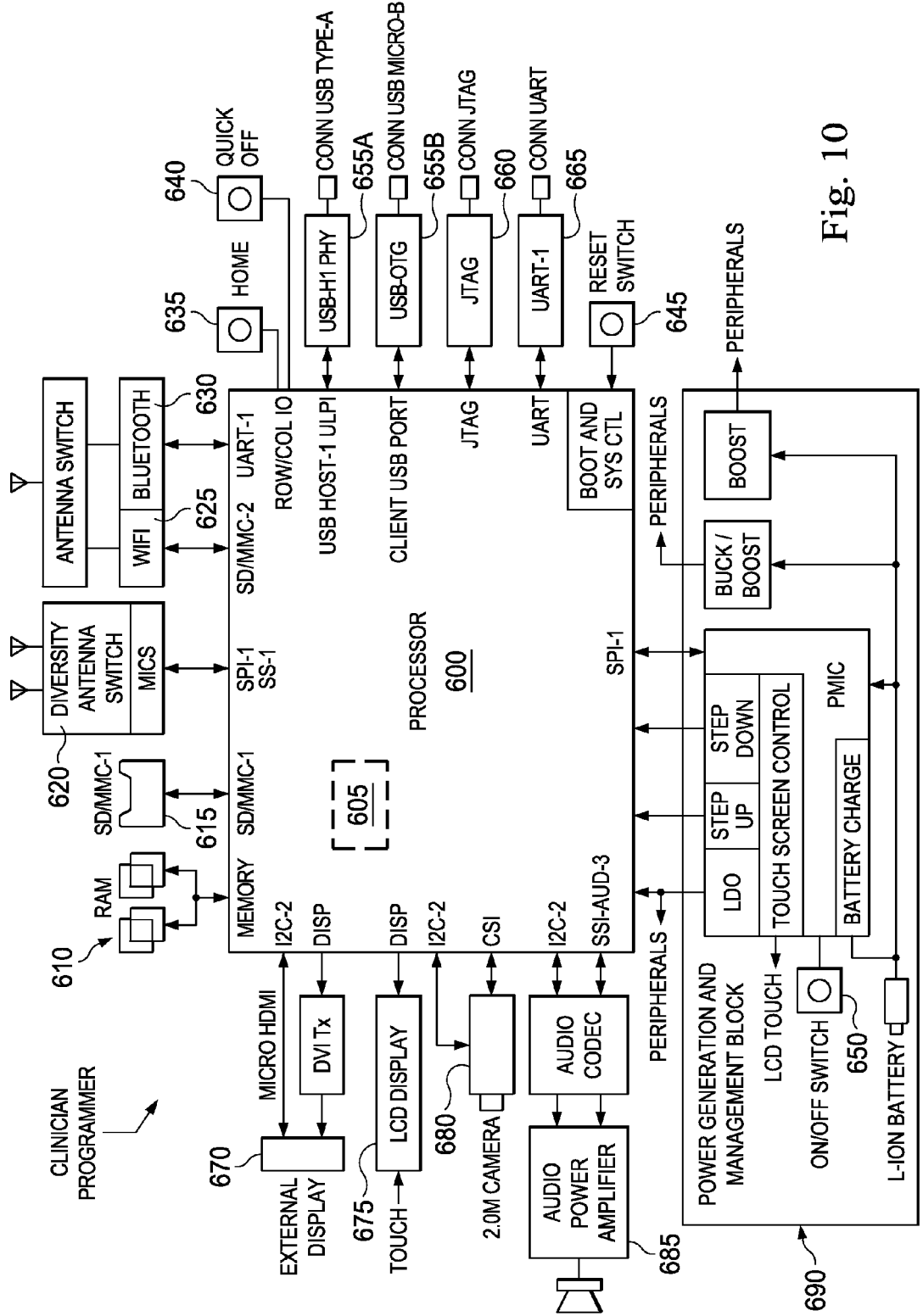
FIG. 10 is a simplified block diagram of an electronic programmer according to various aspects of the present disclosure.

FIG. 10 shows a block diagram of one embodiment of the electronic programmer (CP) discussed herein. For example, the electronic programmer may be a clinician programmer (CP) configured to determine the electrode configuration and positioning discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 10, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 10 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 10.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 10.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 10) may also be included for data transfer.

It is understood that a patient programmer may be implemented in a similar manner as the clinician programmer shown in FIG. 10.

Figure 11:
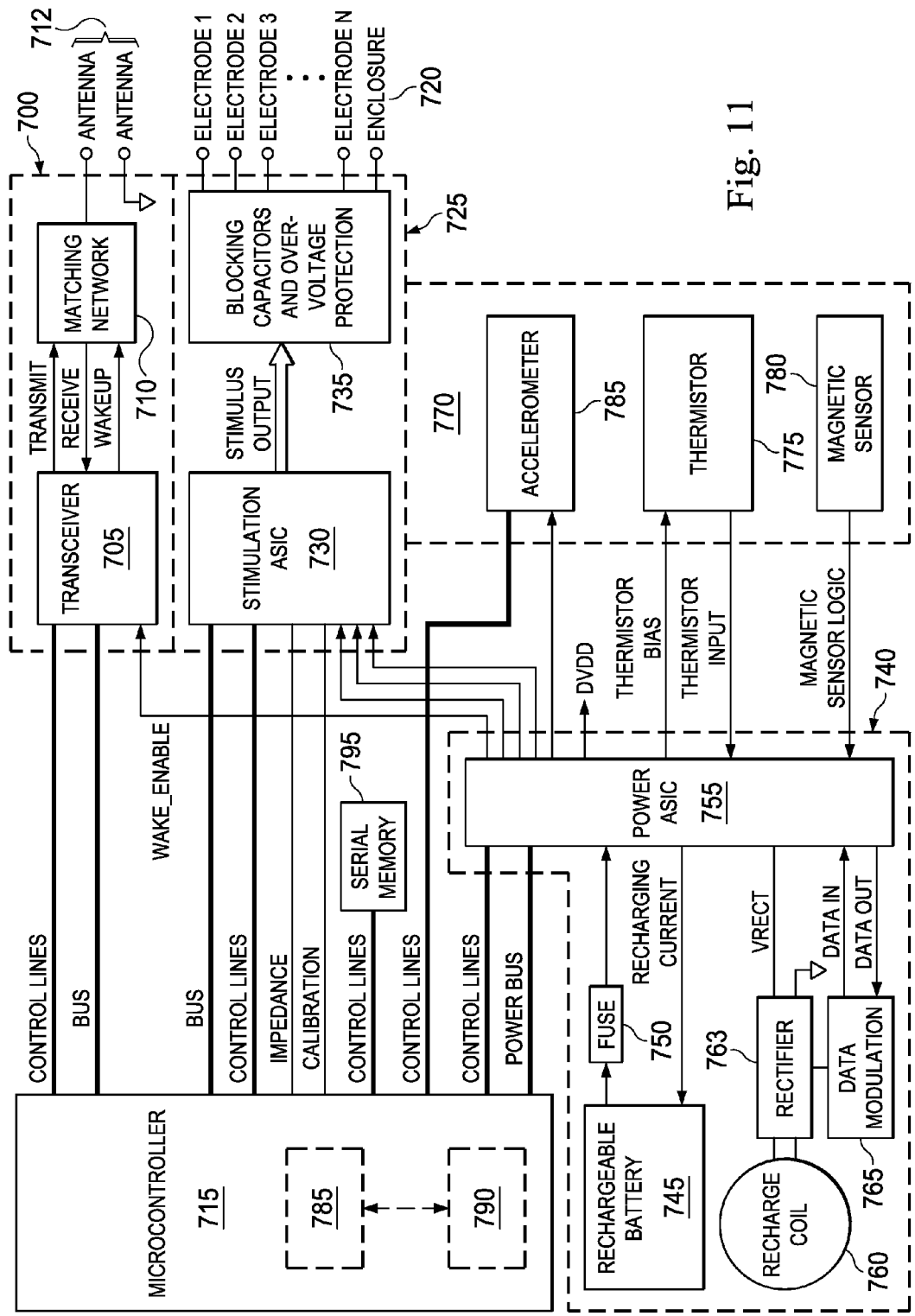
FIG. 11 is a simplified block diagram of an implantable medical device according to various aspects of the present disclosure.

FIG. 11 shows a block diagram of one embodiment of an implantable medical device. In the embodiment shown in FIG. 11, the implantable medical device includes an implantable pulse generator (IPG). The IPG includes a printed circuit board ("PCB") that is populated with a plurality of electrical and electronic components that provide power, operational control, and protection to the IPG. With reference to FIG. 11, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 11, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 11 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 12:
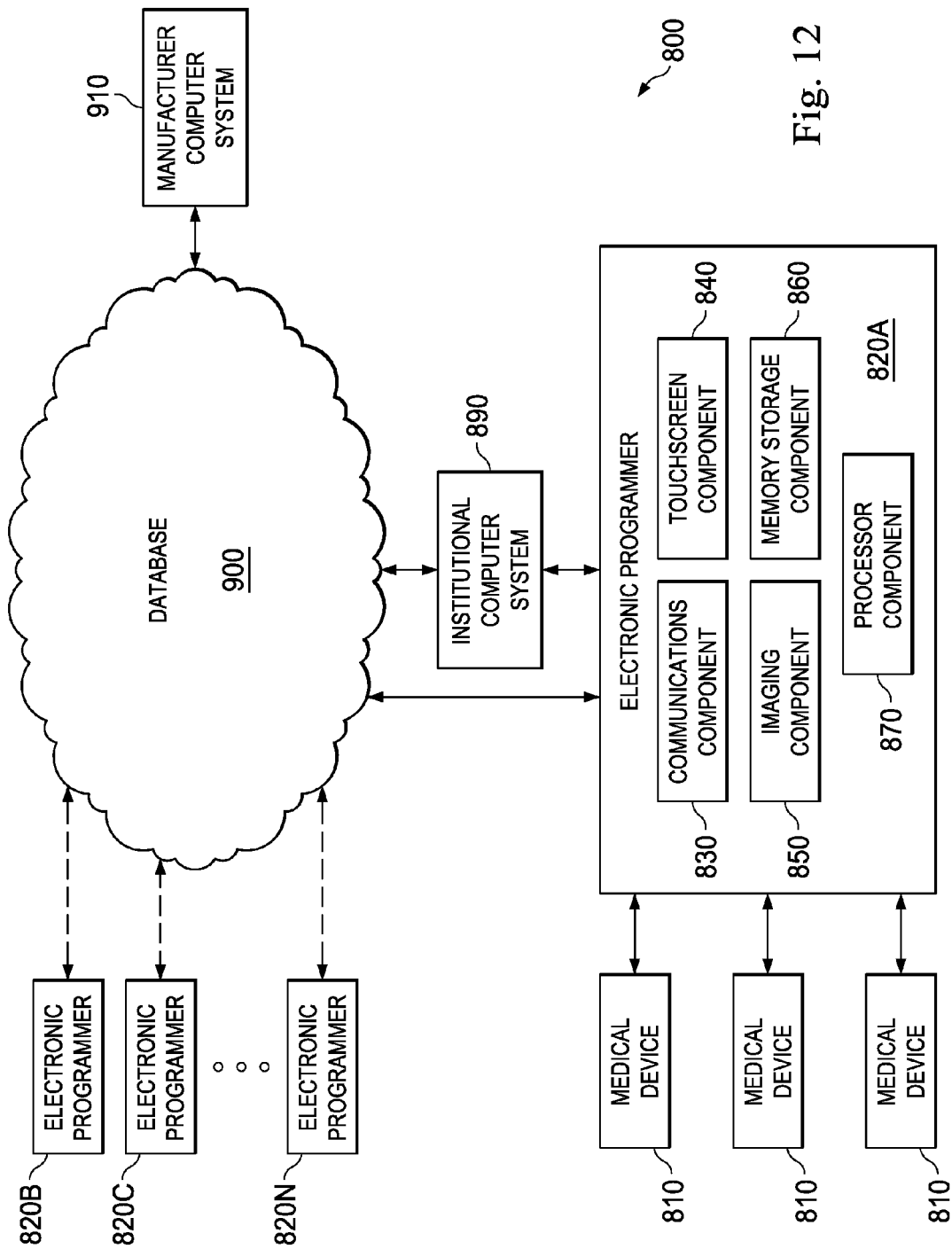
FIG. 12 is a simplified block diagram of a medical system/infrastructure according to various aspects of the present disclosure.

Referring now to FIG. 12, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 11), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 10. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 12 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, electronic data, such as pain and stimulation maps (collectively referred to as sensation maps) may be uploaded from the electronic programmer 820A to the database 900. The sensation maps are discussed in more detail in provisional U.S. Patent Application No. 61/695,407, filed on Aug. 31, 2012, entitled "Method and System of Producing 2D Representations of 3D Pain and Stimulation Maps and Implant Models on a Clinician Programmer," and provisional U.S. Patent Application No. 61/695,721, filed on Aug. 31, 2012, entitled "Method and System of Creating, Displaying, and Comparing Pain and Stimulation Maps," and provisional U.S. Patent Application No. 61/695,676, filed on Aug. 31, 2012, entitled "Method and System of Adjusting 3D Models of Patients on a Clinician Programmer," the disclosure of each of which is hereby incorporated by reference in its entirety.

The sensation maps saved in the database 900 may thereafter be downloaded by any of the other electronic programmers 820B-820N communicatively coupled to it, assuming the user of these programmers has the right login permissions. For example, after the 2D sensation map is generated by the electronic programmer 820A and uploaded to the database 900. That 2D sensation map can then be downloaded by the electronic programmer 820B, which can use the downloaded 2D sensation map to reconstruct or recreate a 3D sensation map. In this manner, a less data-intensive 2D sensation map may be derived from a data-heavy 3D sensation map, sent to a different programmer through the database, and then be used to reconstruct the 3D sensation map. The sensation maps are used herein merely as an example to illustrate the transfer of electronic data in the medical infrastructure 800. Other types of electronic data may also be transferred in a similar (or different) manner.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 13A:
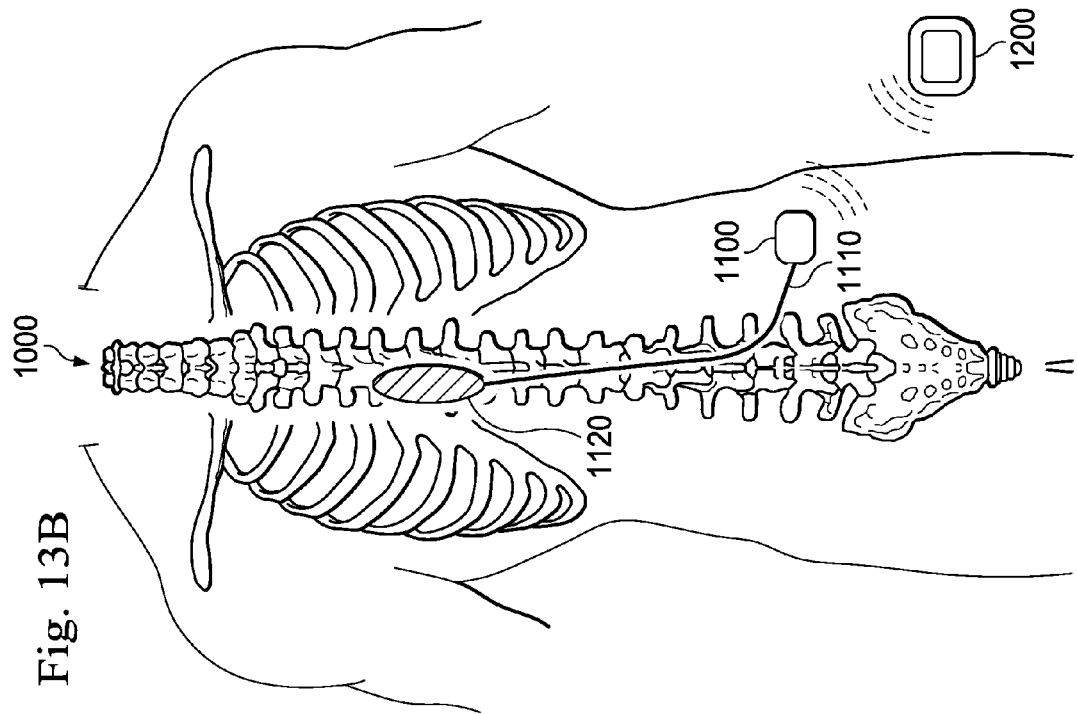
FIGS. 13A and 13B are side and posterior views of a human spine, respectively.
Figure 13B:
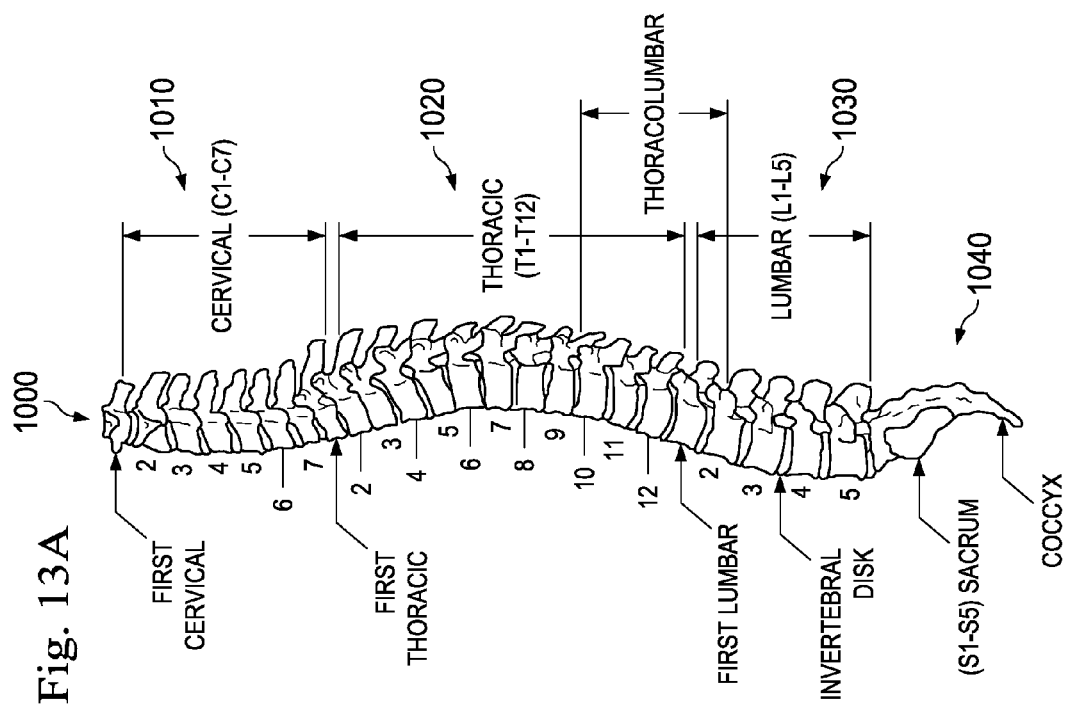

FIG. 13A is a side view of a spine 1000, and FIG. 13B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 13B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 10.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device for determining electrode configuration and positioning for neurostimulation, the electronic device comprising:
   a memory storage component configured to store programming code; and
   a computer processor configured to execute the programming code to perform the following tasks:
      providing, at least in part via a graphical user interface, a virtual representation of an implant lead, the implant lead being configured to deliver electrical stimulation to a patient via one or more of a plurality of electrodes located on the implant lead;

providing, at least in part via the graphical user interface, a plurality of unique predefined electrode activation patterns, wherein each of the predefined electrode activation patterns identifies and displays a plurality of subsets of the electrodes that can be activated one subset at a time, wherein the electrodes in each subset are programmed, by the computer processor, with their respective electrical stimulation parameters;

receiving a user selection of one of the predefined electrode activation patterns;

visually indicating on the virtual representation of the implant lead, which electrodes correspond to one of the plurality of the subset of the electrodes of the user selected predefined electrode activation pattern when a particular subset is user selected; and activating the subsets of the electrodes of the user selected predefined electrode activation pattern one subset at a time, wherein each activated subset of electrodes is adapted to deliver electrical stimulation to a different region of a spine of the patient.

2. The electronic device of claim 1, wherein the tasks further comprise:
receiving patient feedback for the activating of each subset of electrodes.

3. The electronic device of claim 2, wherein the tasks further comprise:
recommending a locational adjustment of the implant lead in response to the activating and the patient feedback.

4. The electronic device of claim 3, wherein the recommending comprises:
identifying, based on the patient feedback, a region of the spine that offers the most pain reduction for the patient; and
recommending the locational adjustment of the implant lead in a manner such that one or more electrodes located near a center of the implant lead are aligned with the region of the spine that offers the most pain reduction for the patient.

5. The electronic device of claim 1, wherein the activating comprises automatically activating the subsets of the electrodes of the user selected predefined electrode activation pattern according to a plurality of predefined sequence steps, and wherein a different subset of electrodes is activated at each sequence step.

6. The electronic device of claim 5, wherein the activating comprises activating the subsets of electrodes are activated consecutively along a direction.

7. The electronic device of claim 1, wherein the tasks further comprise:
displaying a virtual control mechanism; and
detecting, from a user, an engagement of the virtual control mechanism;
wherein the activating the subsets of electrodes is performed in response to the detected engagement of the virtual control mechanism.

8. The electronic device of claim 7, wherein the virtual control mechanism comprises one of: a virtual slider, a virtual toggle, or a virtual joystick.

9. The electronic device of claim 1, wherein the providing the plurality of unique predefined electrode activations pattern is performed such that, within each predefined electrode activation pattern, the different subsets of electrodes are segregated by virtual dividers on the virtual representation of the implant lead.

10. The electronic device of claim 1, wherein the electrical stimulation parameters include at least one of: current amplitude, pulse width, frequency, or electrode polarity.

11. The electronic device of claim 1, wherein: the memory storage component and the computer processor are implemented in an portable electronic programmer having a screen, and wherein the providing the virtual representation of the implant lead and the providing the plurality of unique predefined electrode activation pattern comprise simultaneously displaying the virtual representation of the implant lead and the plurality of unique predefined electrode activation patterns on the screen of the portable electronic programmer.

12. The electronic device of claim 11, wherein the tasks further comprise:
displaying, on the screen of the portable electronic programmer, a virtual representation of an anatomical environment containing a portion of the spine of the patient and a disposition of the implant lead with respect to the portion of the spine.

13. The electronic device of claim 1, wherein the tasks further comprise displaying the electrical stimulation parameters for the subset of the electrodes of the user selected predefined electrode activation pattern.

14. A medical system, comprising:
an implantable lead configured to deliver electrical stimulation to a patient via one or more of a plurality of electrodes located on the implantable lead; and
a portable electronic programmer on which a touch-sensitive user interface is implemented, wherein the portable electronic programmer is configured to:
provide, at least in part via the user interface, a virtual representation of the implantable lead;
provide, at least in part via the user interface, a plurality of unique predefined electrode activation patterns, wherein each of the predefined electrode activation patterns identifies and displays a plurality of respective subsets of the electrodes on the implantable lead that can be activated one subset at a time, wherein the electrodes in each subset are programmed, by the portable electronic programmer, with their respective electrical stimulation parameters;
receive a user selection of one of the predefined electrode activation patterns;
visually indicate on the virtual representation of the implantable lead, which electrodes correspond to one of the plurality of the subset of the electrodes of the user selected predefined electrode activation pattern when a particular subset is user selected; and
activate the subsets of the electrodes of the user selected predefined electrode activation pattern one subset at a time, wherein each activated subset of electrodes is adapted to deliver electrical stimulation to a different region of a spine of the patient.

15. The medical system of claim 14, wherein the user interface is configured to activate the subsets of the electrodes during a surgery that implants the implantable lead into the patient.

16. The medical system of claim 14, wherein the user interface is further configured to: receive patient feedback for the activating of each subset of electrodes.

17. The medical system of claim 16, wherein the user interface is further configured to: recommend a locational adjustment of the implantable lead in response to an activation of the subsets of the electrodes and the patient feedback.

18. The medical system of claim 17, wherein the user interface is configured to recommend the locational adjustment by:
identifying, based on the patient feedback, a region of the spine that offers the most pain reduction for the patient; and recommending the locational adjustment of the implantable lead in a manner such that one or more electrodes located near a center of the implantable lead are aligned with the region of the spine that offers the most pain reduction for the patient.

19. The medical system of claim 14, wherein the user interface is configured to activate the subsets of the electrodes of the user selected predefined electrode activation pattern by automatically activating the subsets of the electrodes according to a plurality of predefined sequence steps, and wherein a different subset of electrodes is activated at each sequence step.

20. The medical system of claim 19, wherein the subsets of electrodes in the user selected predefined electrode activation pattern are activated consecutively along a direction.

21. The medical system of claim 14, wherein the user interface is further configured to:
    display a virtual control mechanism; and
    detect, from a user, an engagement of the virtual control mechanism;
    wherein the user interface is configured to activate the subsets of electrodes in the user selected predefined electrode activation pattern in response to the detected engagement of the virtual control mechanism.

22. The medical system of claim 21, wherein the virtual control mechanism comprises one of: a virtual slider, a virtual toggle, or a virtual joystick.

23. The medical system of claim 14, wherein the user interface is configured to provide the predefined electrode activation pattern in a manner such that the different subsets of electrodes in each predefined electrode activation pattern are segregated by virtual dividers on the virtual representation of the implantable lead.

24. The medical system of claim 14, wherein the electrical stimulation parameters include at least one of: current amplitude, pulse width, frequency, or electrode polarity.

25. The medical system of claim 14, wherein the user interface is configured to simultaneously display the virtual representation of the implantable lead and the plurality of predefined electrode activation patterns on a screen of the portable electronic programmer.

26. The medical system of claim 25, wherein the user interface is further configured to: display, on the screen of the portable electronic programmer, a virtual representation of an anatomical environment containing a portion of the spine of the patient and a disposition of the implantable lead with respect to the portion of the spine.

27. The medical system of claim 14, wherein the portable electronic programmer is further configured to display the electrical stimulation parameters for the subset of the electrodes of the user selected predefined electrode activation pattern.

28. A method of determining electrode configuration and positioning for neurostimulation, the method comprising:
    providing, at least in part via a graphical user interface, a virtual representation of an implant lead, the implant lead being configured to deliver electrical stimulation to a patient via one or more of a plurality of electrodes located on the implant lead;
    providing, at least in part via the graphical user interface, a plurality of unique predefined electrode activation patterns, wherein each of the predefined electrode activation patterns identifies and displays a plurality of subsets of the electrodes that can be activated one subset at a time, wherein the electrodes in each subset are programmed, by the computer processor, with their respective electrical stimulation parameters;
    receiving a user selection of one of the predefined electrode activation patterns;
    visually indicating on the virtual representation of the implant lead, which electrodes correspond to one of the plurality of the subset of the electrodes of the user selected predefined electrode activation pattern when a particular subset is user selected; and
    activating the subsets of the electrodes of the user selected predefined electrode activation pattern one subset at a time, wherein each activated subset of electrodes is adapted to deliver electrical stimulation to a different region of a spine of the patient.

29. The method of claim 28, wherein the activating is performed during a surgery that implants the implant lead into the patient.

30. The method of claim 28, further comprising: receiving patient feedback for the activating of each subset of electrodes.

31. The method of claim 30, further comprising: recommending a locational adjustment of the implant lead in response to the activating and the patient feedback.

32. The method of claim 31, wherein the recommending comprises:
    identifying, based on the patient feedback, a region of the spine that offers the most pain reduction for the patient; and
    recommending the locational adjustment of the implant lead in a manner such that one or more electrodes located near a center of the implant lead are aligned with the region of the spine that offers the most pain reduction for the patient.

33. The method of claim 28, wherein the activating comprises automatically activating the subsets of the electrodes in the user selected predefined electrode activation pattern according to a plurality of predefined sequence steps, and wherein a different subset of electrodes is activated at each sequence step.

34. The method of claim 33, wherein the subsets of electrodes in the user selected predefined electrode activation pattern are activated consecutively along a direction.

35. The method of claim 28, further comprising:
    displaying a virtual control mechanism; and
    detecting, from a user, an engagement of the virtual control mechanism;
    wherein the activating of the subsets of electrodes in the user selected predefined electrode activation pattern is performed in response to the detected engagement of the virtual control mechanism.

36. The method of claim 35, wherein the virtual control mechanism comprises one of: a virtual slider, a virtual toggle, or a virtual joystick.

37. The method of claim 28, wherein the providing the predefined electrode activation pattern is performed such that the different subsets of electrodes in the user selected predefined electrode activation pattern are segregated by virtual dividers on the virtual representation of the implant lead.

38. The method of claim 28, wherein the electrical stimulation parameters include at least one of: current amplitude, pulse width, frequency, or electrode polarity.

39. The method of claim 28, wherein the providing the virtual representation of the implant lead and the providing the predefined electrode activation pattern comprise simultaneously displaying the virtual representation of the implant lead and the plurality of predefined electrode activation patterns on a screen of a clinician programmer.

40. The method of claim 39, further comprising: displaying, on the screen of the clinician programmer, a virtual representation of an anatomical environment containing a portion of the spine of the patient and a disposition of the implant lead with respect to the portion of the spine.

41. The method of claim 28, further comprising displaying the electrical stimulation parameters for the subset of the electrodes of the user selected predefined electrode activation pattern.

42. An electronic apparatus for determining electrode configuration and positioning for neurostimulation, the electronic apparatus comprising:
input/output means for communicating with a user, the input/output means including a touch-sensitive screen configured to detect an input from the user and display an output to the user;
memory storage means for storing executable instructions; and
computer processor means for executing the instructions to perform the following tasks:
providing, at least in part via a graphical user interface, a virtual representation of an implant lead, the implant lead being configured to deliver electrical stimulation to a patient via one or more of a plurality of electrodes located on the implant lead;
providing, at least in part via the graphical user interface, a plurality of unique predefined electrode activation patterns, wherein each of the predefined electrode activation patterns identifies and displays a plurality of subsets of the electrodes that can be activated one subset at a time, wherein the electrodes in each subset are programmed, by the computer processor, with their respective electrical stimulation parameters;
receiving a user selection of one of the predefined electrode activation patterns;
visually indicating on the virtual representation of the implant lead, which electrodes correspond to one of the plurality of the subset of the electrodes of the user selected predefined electrode activation pattern when a particular subset is user selected; and
activating the subsets of the electrodes of the user selected predefined electrode activation pattern one subset at a time, wherein each activated subset of electrodes is adapted to deliver electrical stimulation to a different region of a spine of the patient.

43. The electronic apparatus of claim 42, wherein the tasks further comprise: receiving patient feedback for the activating of each subset of electrodes.

44. The electronic apparatus of claim 43, wherein the tasks further comprise: recommending a locational adjustment of the implant lead in response to the activating and the patient feedback.

45. The electronic apparatus of claim 44, wherein the recommending comprises:
identifying, based on the patient feedback, a region of the spine that offers the most pain reduction for the patient; and
recommending the locational adjustment of the implant lead in a manner such that one or more electrodes located near a center of the implant lead are aligned with the region of the spine that offers the most pain reduction for the patient.

46. The electronic apparatus of claim 42, wherein the activating comprises automatically activating the subsets of the electrodes of the user selected predefined electrode activation pattern according to a plurality of predefined sequence steps, and wherein a different subset of electrodes is activated at each sequence step.

47. The electronic apparatus of claim 46, wherein the subsets of electrodes of the user selected predefined electrode activation pattern are activated consecutively along a direction.

48. The electronic apparatus of claim 42, wherein the tasks further comprise:
displaying a virtual control mechanism; and
detecting, from a user, an engagement of the virtual control mechanism;
wherein the activating the subsets of electrodes of the user selected predefined electrode activation pattern is performed in response to the detected engagement of the virtual control mechanism.

49. The electronic apparatus of claim 48, wherein the virtual control mechanism comprises one of: a virtual slider, a virtual toggle, or a virtual joystick.

50. The electronic apparatus of claim 42, wherein the providing the predefined electrode activation pattern is performed such that the different subsets of electrodes of the user selected predefined electrode activation pattern are segregated by virtual dividers on the virtual representation of the implant lead.

51. The electronic apparatus of claim 42, wherein the electrical stimulation parameters include at least one of: current amplitude, pulse width, frequency, or electrode polarity.

52. The electronic apparatus of claim 42, wherein the input/output means comprises a screen, and wherein the providing the virtual representation of the implant lead and the providing the predefined electrode activation pattern comprise simultaneously displaying the virtual representation of the implant lead and the plurality of predefined electrode activation patterns on the screen.

53. The electronic apparatus of claim 52, wherein the tasks further comprise: displaying, on the screen, a virtual representation of an anatomical environment containing a portion of the spine of the patient and a disposition of the implant lead with respect to the portion of the spine.

54. The electronic apparatus of claim 42, wherein the tasks further comprise displaying the electrical stimulation parameters for the subset of the electrodes of the user selected predefined electrode activation pattern.

\* \* \* \* \*